US012690974B2

(12) United States Patent
Ginn et al.

(10) Patent No.: US 12,690,974 B2
(45) Date of Patent: Jul. 28, 2026

(54) SYSTEMS, APPARATUS AND METHODS FOR STABILIZING BONE STRUCTURES

(71) Applicant: Tenon Medical, Inc., Los Gatos, CA (US)

(72) Inventors: Richard S Ginn, Gilroy, CA (US); Richard Brown, Colorado Springs, CO (US)

(73) Assignee: Tenon Medical, Inc., Los Gatos, CA (US)

( * ) Notice: Subject to any disclaimer, the term of this patent is extended or adjusted under 35 U.S.C. 154(b) by 1002 days.

(21) Appl. No.: 17/899,926

(22) Filed: Aug. 31, 2022

(65) Prior Publication Data

US 2023/0000630 A1 Jan. 5, 2023

Related U.S. Application Data

(63) Continuation-in-part of application No. 17/833,960, filed on Jun. 7, 2022, which is a continuation-in-part
(Continued)

(51) Int. Cl.
*A61F 2/30* (2006.01)
*A61B 5/055* (2006.01)
(Continued)

(52) U.S. Cl.
CPC .......... *A61F 2/30988* (2013.01); *A61B 5/055* (2013.01); *A61B 5/062* (2013.01); *A61B 6/032* (2013.01); *A61B 6/485* (2013.01); *A61B 8/0841* (2013.01); *A61B 17/1604* (2013.01); *A61B 17/1664* (2013.01); *A61B 17/1671*

(2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01); (Continued)

(58) Field of Classification Search
CPC ... A61B 17/7055; A61B 17/7001–7046; A61F 2002/30995; A61F 2/30988; A61F 2/4455–447
See application file for complete search history.

(56) References Cited

U.S. PATENT DOCUMENTS 5,127,912 A * 7/1992 Ray .................... A61B 17/7055
606/250
5,300,073 A * 4/1994 Ray .................... A61B 17/7041
606/250
(Continued)

*Primary Examiner* — Lynnsy M Summitt
(74) *Attorney, Agent, or Firm* — Francis Law Group

(57) ABSTRACT

A musculoskeletal stabilization system adapted to stabilize spine and SI joint structures. The musculoskeletal stabilization system includes a spine structure stabilization sub-system and a pelvic structure stabilization sub-system. The pelvic structure stabilization sub-system comprising two multi-function prostheses that are adapted to be delivered to and inserted into SI joints of a subject via a posterior trajectory. The multi-function joint prostheses are further adapted to stabilize respective SI joints and cooperate with the spine stabilization sub-system to also stabilize the subject's spine jointly.

7 Claims, 29 Drawing Sheets

Related U.S. Application Data of application No. 17/833,098, filed on Jun. 6, 2022, now Pat. No. 12,551,348, which is a continuation of application No. 17/749,199, filed on May 20, 2022, now Pat. No. 12,465,491, which is a continuation-in-part of application No. 17/740,568, filed on May 10, 2022, now Pat. No. 12,472,069, which is a continuation-in-part of application No. 17/463,779, filed on Sep. 1, 2021, now Pat. No. 12,427,027, which is a continuation-in-part of application No. 13/857,977, filed on Apr. 5, 2013, now Pat. No. 11,273,042, which is a continuation of application No. 13/192,289, filed on Jul. 27, 2011, now abandoned.

(60) Provisional application No. 61/368,233, filed on Jul. 27, 2010.

(51) Int. Cl.

| | | |
|---|---|---|
| *A61B 5/06* | (2006.01) | |
| *A61B 6/00* | (2006.01) | |
| *A61B 6/03* | (2006.01) | |
| *A61B 8/08* | (2006.01) | |
| *A61B 17/16* | (2006.01) | |
| *A61B 17/70* | (2006.01) | |
| *A61B 17/88* | (2006.01) | |
| *A61B 34/20* | (2016.01) | |
| *A61F 2/44* | (2006.01) | |
| *A61F 2/46* | (2006.01) | |

(52) U.S. Cl.

CPC ............... *A61F 2002/30166* (2013.01); *A61F 2002/30593* (2013.01); *A61F 2002/30995* (2013.01)

(56) References Cited

U.S. PATENT DOCUMENTS

| | | | | | |
|---|---|---|---|---|---|
| 5,591,235 | A | * | 1/1997 | Kuslich | A61B 17/701 |
| | | | | | 606/279 |
| 5,601,554 | A | * | 2/1997 | Howland | A61B 17/7049 |
| | | | | | 606/252 |
| 5,683,391 | A | * | 11/1997 | Boyd | A61B 17/7032 |
| | | | | | 606/279 |
| 5,704,936 | A | * | 1/1998 | Mazel | A61B 17/7044 |
| | | | | | 606/255 |
| 6,159,211 | A | * | 12/2000 | Boriani | A61F 2/4455 |
| | | | | | 606/279 |
| 6,325,805 | B1 | * | 12/2001 | Ogilvie | A61B 17/0642 |
| | | | | | 606/911 |
| 7,909,871 | B2 | * | 3/2011 | Abdou | A61B 17/70 |
| | | | | | 606/264 |
| 8,562,651 | B2 | * | 10/2013 | Metcalf | A61B 17/869 |
| | | | | | 606/264 |
| 8,641,737 | B2 | * | 2/2014 | Matthis | A61B 17/7038 |
| | | | | | 606/265 |
| 8,668,721 | B2 | * | 3/2014 | Miller | A61B 17/7055 |
| | | | | | 606/264 |
| 8,808,377 | B2 | * | 8/2014 | Donner | A61F 2/4455 |
| | | | | | 623/17.11 |
| 8,808,379 | B2 | * | 8/2014 | Abdou | A61B 17/702 |
| | | | | | 623/17.11 |
| 8,852,241 | B2 | * | 10/2014 | Datta | A61B 17/7049 |
| | | | | | 606/279 |
| 8,951,254 | B2 | * | 2/2015 | Mayer | A61B 17/1617 |
| | | | | | 623/18.11 |
| 9,333,090 | B2 | * | 5/2016 | Donner | A61B 17/7055 |
| 9,381,045 | B2 | * | 7/2016 | Donner | A61B 17/7055 |
| 9,387,013 | B1 | * | 7/2016 | Shoshtaev | A61B 17/7056 |
| 9,421,109 | B2 | * | 8/2016 | Donner | A61B 17/844 |
| 9,579,127 | B2 | * | 2/2017 | Kostuik | A61B 17/7037 |
| 9,585,756 | B2 | * | 3/2017 | Mayer | A61B 17/70 |
| 9,700,356 | B2 | * | 7/2017 | Donner | A61B 17/86 |
| 9,717,539 | B2 | * | 8/2017 | Donner | A61B 17/7055 |
| 9,788,961 | B2 | * | 10/2017 | Donner | A61B 17/7055 |
| 9,826,986 | B2 | * | 11/2017 | Donner | A61B 17/7055 |
| 9,888,911 | B2 | * | 2/2018 | Siegal | A61B 17/025 |
| 10,245,076 | B2 | * | 4/2019 | Fitzpatrick | A61B 34/10 |
| 10,245,087 | B2 | * | 4/2019 | Donner | A61B 17/808 |
| 10,433,880 | B2 | * | 10/2019 | Donner | A61B 17/7049 |
| 10,596,004 | B2 | * | 3/2020 | Donner | A61B 17/1626 |
| 10,603,055 | B2 | * | 3/2020 | Donner | A61B 17/1739 |
| 10,751,188 | B2 | * | 8/2020 | Guo | A61B 17/7032 |
| 11,752,011 | B2 | * | 9/2023 | Stuart | A61F 2/447 |
| | | | | | 623/17.11 |
| 11,857,420 | B2 | * | 1/2024 | Mullin | A61F 2/2846 |
| 11,872,141 | B2 | * | 1/2024 | Lee | A61B 17/8875 |
| 12,496,108 | B2 | * | 12/2025 | Holton | A61B 17/1757 |
| 2004/0147929 | A1 | * | 7/2004 | Biedermann | A61B 17/864 |
| | | | | | 623/17.11 |
| 2008/0021454 | A1 | * | 1/2008 | Chao | A61B 17/7044 |
| | | | | | 606/250 |
| 2008/0021456 | A1 | * | 1/2008 | Gupta | A61B 17/7049 |
| | | | | | 606/250 |
| 2012/0253398 | A1 | | 10/2012 | Metcalf et al. | |
| 2013/0085534 | A1 | * | 4/2013 | Hainard | A61B 17/7044 |
| | | | | | 606/278 |
| 2013/0184760 | A1 | * | 7/2013 | Ballard | A61B 17/7038 |
| | | | | | 606/279 |
| 2013/0253519 | A1 | * | 9/2013 | Mitchell | A61B 17/863 |
| | | | | | 606/80 |
| 2021/0393409 | A1 | * | 12/2021 | Ginn | A61B 17/92 |
| 2022/0071644 | A1 | * | 3/2022 | Donner | A61B 17/144 |
| 2024/0180710 | A1 | * | 6/2024 | Peretz | A61F 2/30988 |
| 2025/0000657 | A1 | * | 1/2025 | Sansur | A61B 17/8875 |
| 2025/0366996 | A1 | * | 12/2025 | Geist | A61B 17/864 |

* cited by examiner $C_1$-$C_7$ $T_1$-$T_{12}$ $L_1$-$L_5$ $S_1$-$S_5$

500a 502
510
502
510
504
502
510
110    110
502L
502R
510
510

502
520
506
518
110
519
512
514
510

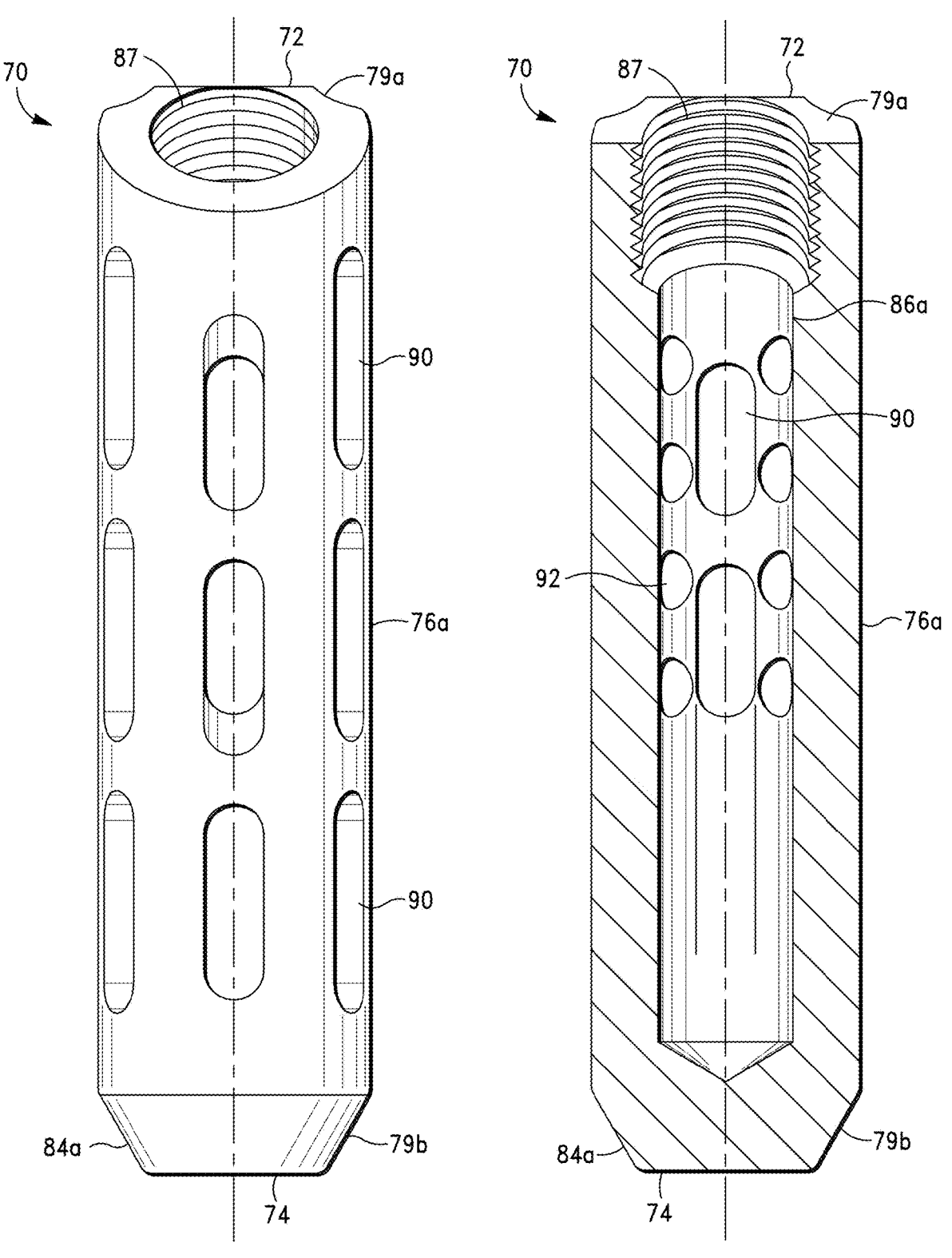
*FIG. 4E*          *FIG. 4F*

SYSTEMS, APPARATUS AND METHODS FOR STABILIZING BONE STRUCTURES

CROSS-REFERENCES TO RELATED APPLICATIONS

This application is a continuation-in-part of U.S. application Ser. No. 17/833,960, filed Jun. 7, 2022, which is a continuation-in-part of U.S. application Ser. No. 17/833,098, filed Jun. 6, 2022, which is a continuation of U.S. patent application Ser. No. 17/749,199, filed on May 20, 2022, which is a continuation-in-part application of U.S. patent application Ser. No. 17/740,568, filed on May 10, 2022, which is a continuation-in-part application of U.S. patent application Ser. No. 17/463,779, filed Sep. 1, 2021, which is a continuation-in part of U.S. patent application Ser. No. 13/857,977, filed Apr. 5, 2013, now U.S. Pat. No. 11,273, 042, which is a continuation application of U.S. patent application Ser. No. 13/192,289, filed Jul. 27, 2011, now abandoned, which claims the benefit of U.S. provisional patent application Ser. No. 61/368,233, filed Jul. 27, 2010.

FIELD OF THE INVENTION

The present invention relates to systems, apparatus and methods for stabilizing dysfunctional bone structures. More particularly, the present invention relates to systems, apparatus and methods for stabilizing dysfunctional spinal and pelvic structures.

BACKGROUND OF THE INVENTION

As is well known in the art, the human spine generally comprises the cervical vertebrae, thoracic vertebrae, lumbar vertebrae, and sacral vertebrae. As illustrated in FIG. 1A, the noted vertebrae comprise the following bone structures:

| Structures of Spine | |
|---|---|
| Cervical Vertebrae | $C_1$—$C_7$ |
| Thoracic Vertebrae | $T_1$—$T_{12}$ |
| Lumbar Vertebrae | $L_1$—$L_5$ |
| Sacral Vertebrae | $S_1$—$S_5$ |

As illustrated in FIG. 1B, the spine further comprises a lumbosacral joint (denoted "1" in FIG. 1B), which is defined by the L5 and S1 bone structures.

As is also well known in the art, the sacroiliac (SI) joint 6 comprises a diarthrodial synovial joint, which, as illustrated in FIG. 2A, is defined by the interface between the articular surfaces of the sacrum 2 and the ilium 4. Thus, the SI joint 6 is defined by (and, hence, comprises) portions of the sacrum 2 and ilium 4.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 2A, is disposed in the interior regions of the sacrum and ilium 2, 4.

As illustrated in FIGS. 2B-2D, the SI joint 6 generally comprises the shape of an inverted capital letter "L" (denoted "13") lying on its side (rather than a triangle), where the long arm of the inverted "L" 15 (i.e., SI joint 6) is oriented along the posterior wall of the pelvis 11 (denoted "25" in FIG. 2A) and is also oriented relatively straight through its entire course. The sacral floor (denoted "21" in FIG. 2C), which is defined by the region between the anterior sacral promontory 19a and the apex 19b of the sacrum 2, generally slopes downward and laterally at an approximately 30% grade relative to the cephalocaudal axis 27.

As further illustrated in FIGS. 2B and 2C, the short arm of the inverted "L" (denoted "17") is generally oriented parallel to the transverse plane of the L5-S1 lumbosacral joint and limited superiorly by the sacral ala (denoted "23" in FIG. 2C) and the apex of the inverted "L" (denoted "29" in FIG. 2B) is positioned below the S2 segment region of the sacrum 2 (denoted "S2") proximate to the S3 segment region of the sacrum 2 (denoted "S3").

As is also well known in the art, the SI joint further comprises articular cartilage, i.e., hyaline and fibrocartilage, and a strong, extensive ligamentous architecture, which stabilizes the SI joint.

As is further well known in the art, the SI joint performs several seminal biomechanical functions; the seminal functions comprising attenuation of loads exerted on the upper body and distribution of the loads to the lower extremities. The SI joint also functions as a shock absorber for loads exerted on spine.

As is well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures.

SI joint dysfunction, and pain associated therewith, is also a common complication associated with spinal deformity and, in many instances spinal deformity correction procedures. Indeed, it is estimated that approximately 75% of subjects that have presented with a spinal deformity and have undergone a spinal deformity correction procedure comprising a spinal stabilization apparatus develop SI joint dysfunction due to increased stress at the SI joint.

As is well known in the art, spinal deformity correction procedures are particularly complex procedures, and achieving adequate spinal deformity correction while avoiding post-operative complications associated therewith is often incredibly challenging.

A common seminal complication associated with spinal deformity correction procedures that often results in the development of SI joint dysfunction is pseudarthrosis, i.e., failure of adjacent bone structures to fuse; particularly, adjacent bone structure proximate the distal end of an employed spinal stabilization apparatus. Indeed, pseudarthrosis often necessitates subsequent surgeries to address the failed fusion event.

Since pseudarthrosis typically occurs at the lumbosacral (L5-S1) joint due to the elevated lever arm of proximally fused bone structure regions and associated cantilevering events, spinal stabilization apparatus have recently incorporated spinopelvic stabilization functionality to provide increased stabilization proximate to the lumbosacral joint to abate pseudarthrosis at the lumbosacral joint.

Various spinal stabilization systems having spine and pelvic stabilization functionality (referred to hereinafter as "musculoskeletal stabilization systems" and "spinopelvic stabilization systems") have thus been developed and employed to abate pseudarthrosis.

One commonly employed spinopelvic stabilization system comprises S2-alar-iliac (S2AI) screws, which are positioned in a region between the sacral neuroforamina of S1 and S2 and driven into the ilium to affix the sacrum to the ilium, such as the S2AI screws "AI$_1$" and "AI$_2$" shown in FIG. 1C.

There are, however, numerous drawbacks and disadvantages associated with the use of S2AI screws; such disadvantages include increased surgical difficulty associated with implantation of the screws, potential pelvic breach upon implantation of the screws, excessive screw bending of the screws in situ, provision of insufficient fixation strength at the SI joint, substantial implant prominence or protrusion, and/or tissue damage.

Indeed, it is estimated that in situ failure of S2AI screws occurs in approximately 10% of spinal deformity correction cases involving spinopelvic stabilization with S2AI screws.

Improved spinopelvic stabilization systems employing S2AI screws, such as the iFuse Bedrock™ system disclosed in U.S. Pub. No. 2020/0261240 to Mesiwala, et al., and the JCBD systems disclosed in U.S. Pat. No. 11,129,718 to Donner, et al., have thus been developed to address the noted disadvantages associated with S2AI screws. Although the noted systems and associated spinopelvic stabilization methods have garnered some success in reinforcing the S2AI screws and, thereby, effectively addressing some of the disadvantages associated with S2AI screws, there similarly remains many disadvantages associated with the systems.

A major disadvantage associated with many of the improved spinopelvic stabilization systems; particularly, the iFuse Bedrock™ and JCBD systems, is that such systems are quite complex and add additional complexity to spinal deformity correction procedures. It has thus been found that, notwithstanding the level of surgical training and experience that a surgeon may possess, when such S2AI screw-based spinopelvic stabilization systems are employed, there are still substantial incidences of damage to the lumbosacral nerve structures proximate to the SI joint and pelvic breach.

A further disadvantage associated with many of the improved spinopelvic stabilization systems, including the iFuse Bedrock™ and JCBD systems, is that such S2AI screw-based systems merely reinforce the S2AI screws via additional components, such as additional prostheses. The additional prostheses are typically positioned in the limited space between the neuroforamen of the sacrum and, hence, associated nerve structures proximate thereto, which increases the probability of damaging the nerve structures and inducing post-operative pain.

The additional components also enhance the system complexity and substantially increase the probability of system failure, and, therefore further surgical procedures to address such failure.

A further disadvantage associated with many of the improved spinopelvic stabilization systems, including the iFuse Bedrock™ and JCBD systems, is that such systems are also often prone to failure due to ineffective engagement of the prostheses in and, thus, to SI joint bone structures and, hence, dislodgement of the prostheses.

It would thus be desirable to provide spinopelvic, i.e., musculoskeletal, stabilization systems apparatus, and methods that substantially reduce or eliminate the disadvantages associated with conventional musculoskeletal stabilization systems, apparatus and methods.

It is therefore an object of the invention to provide musculoskeletal stabilization systems, apparatus and methods that substantially reduce or eliminate the disadvantages associated with conventional musculoskeletal stabilization systems, apparatus and methods.

It is another object of the invention to provide musculoskeletal stabilization systems and apparatus, and methods employing same, which effectively stabilize dysfunctional spine bone structures.

It is another object of the invention to provide musculoskeletal stabilization systems and apparatus, and methods employing same, which effectively ameliorate pain associated with spine bone structure dysfunction.

It is another object of the invention to provide musculoskeletal stabilization systems and apparatus, and methods employing same, which effectively stabilize dysfunctional pelvic bone structures.

It is another object of the invention to provide musculoskeletal stabilization systems and apparatus, and methods employing same, which effectively ameliorate pain associated with pelvic bone structure dysfunction; particularly, SI joint dysfunction.

It is another object of the invention to provide musculoskeletal stabilization systems and apparatus, and methods employing same, which effectively stabilize dysfunctional spine and pelvic bone structures.

It is another object of the invention to provide musculoskeletal stabilization systems and apparatus, and methods employing same, which effectively ameliorate pain associated with spine and pelvic bone structure dysfunction.

It is another object of the invention to provide improved musculoskeletal stabilization systems comprising prostheses adapted to induce remodeling of damaged osseous tissue and regeneration of new osseous tissue.

SUMMARY OF THE INVENTION

The present invention is directed to systems and apparatus for stabilizing bone structures (referred to hereinafter as "musculoskeletal stabilization systems and apparatus"), and methods employing same.

In one embodiment of the invention, there is thus provided a musculoskeletal stabilization system for stabilizing spine and pelvic bone structures presenting with an abnormality or impairment, i.e., dysfunction.

In one embodiment, the noted musculoskeletal stabilization system comprises a spine structure stabilization sub-system and a pelvic structure stabilization sub-system, the spine structure stabilization sub-system comprising a plurality of bone-engaging anchoring assemblies, and first and second elongate stabilizing rods, each of the plurality of bone-engaging anchoring assemblies adapted to engage vertebral bone structures of the subject's spine, the first and second elongate stabilizing rods adapted to be positioned on opposite sides of the subject's sagittal plane, the pelvic structure stabilization sub-system comprising first and second prosthesis systems, the first prosthesis system comprising a first prosthesis adapted to be delivered to and inserted into the first SI joint of the subject's pelvic structure via a first posterior trajectory, the second prosthesis system comprising a second prosthesis adapted to be delivered to and inserted into the second SI joint of the subject's pelvic structure via a second posterior trajectory, the first and second prostheses comprising first and second elongated partially cylindrical sections connected to a bridge section, the first bridge section comprising a first tapered region adapted to disrupt at least articular cartilage and cortical bone when the first and second joint prostheses are inserted into the first and second SI joints, the first elongated partially cylindrical section comprising a first internal lumen that extends through the first elongated partially cylindrical section, the first internal lumen comprising first internal threads, the second elongated partially cylindrical section comprising a second internal lumen that extends through the second elongated partially cylindrical section, the second internal lumen comprising second internal threads, the first prosthesis further comprising first spine structure stabilization sub-system engagement means adapted to threadably engage at least the first internal threads of the first elongated partially cylindrical section of the first prosthesis and the spine structure stabilization sub-system, the second prosthesis further comprising second spine structure stabilization sub-system engagement means adapted to threadably engage at least the first internal threads of the first elongated partially cylindrical section of the second prosthesis and the spine structure stabilization sub-system.

In a preferred embodiment of the invention, the first spine structure stabilization sub-system engagement means is configured and adapted to engage the first elongate stabilizing rod of the spine structure stabilization sub-system, and the second spine structure stabilization sub-system engagement means of the second prosthesis is configured and adapted to engage the second elongate stabilizing rod of the spine structure stabilization sub-system.

In some embodiments of the invention, at least the first internal lumen of the first elongated partially cylindrical section of the first and second prostheses is adapted to receive an osteogenic composition and/or pharmacological agent therein.

In some embodiments of the invention, at least the first internal lumen of the first elongated partially cylindrical section of the first and second prostheses comprises a first plurality of slots in communication with the first lumen of the first elongated partially cylindrical section, the first plurality of slots being configured and adapted to allow the osteogenic composition and/or pharmacological agent in the first internal lumen to be dispersed out and delivered to the first and second SI joints when the first and second joint prostheses are inserted therein.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 4E is a right-side plan view of the prosthesis shown in FIG. 4A, in accordance with the invention;

FIG. 4F is a right-side sectional plan view of the prosthesis shown in FIG. 4A, in accordance with the invention;

DETAILED DESCRIPTION OF THE PREFERRED EMBODIMENT

Figure 1A:
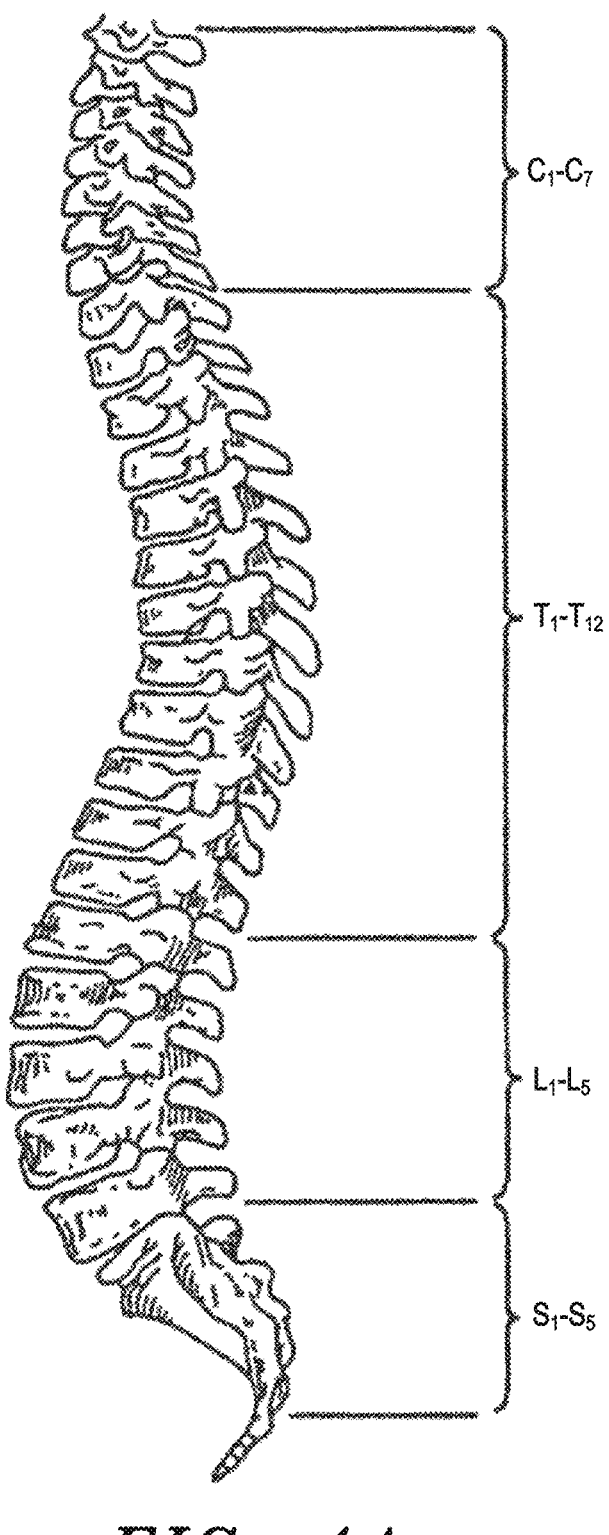
FIG. 1A is a schematic illustration of a human spine.
Figure 1B:
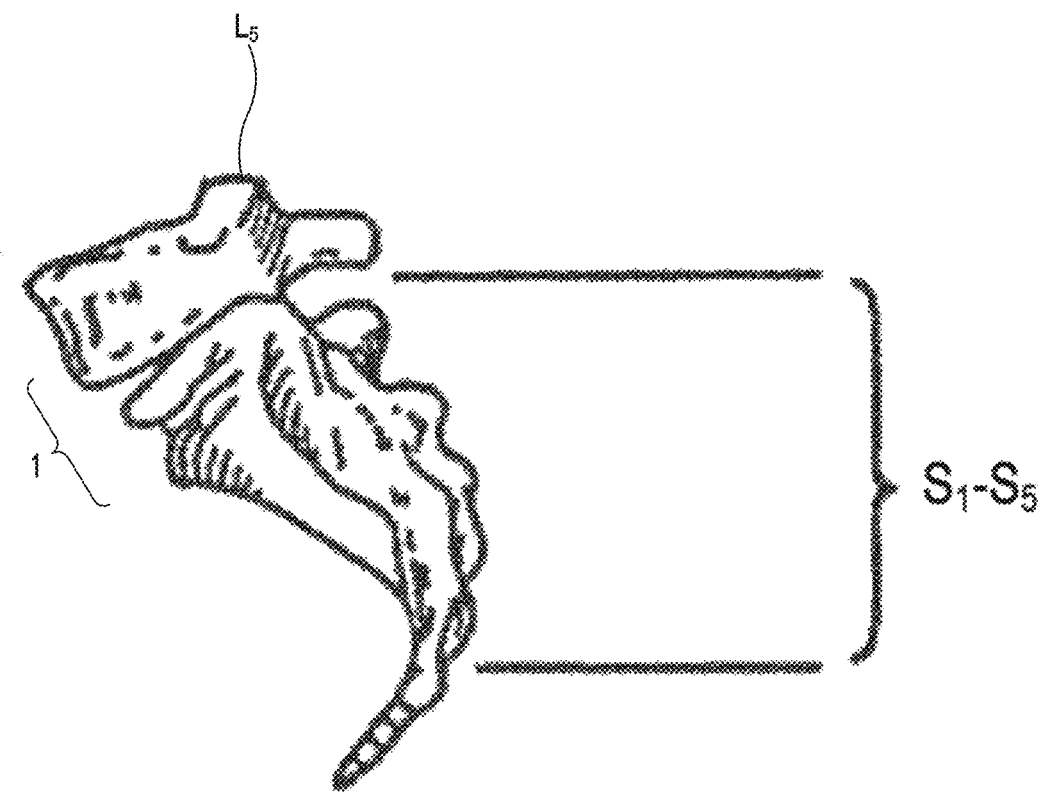
FIG. 1B is a schematic illustration of a lumbosacral joint.
Figure 1C:
FIG. 1C is a computed tomography (CT) scan of a human pelvic region from an inferior perspective showing conventional S2AI screws.

Before describing the present invention in detail, it is to be understood that this invention is not limited to particularly exemplified systems, apparatus, structures or methods as such may, of course, vary. Thus, although a number of systems, apparatus, structures and methods similar or equivalent to those described herein can be used in the practice of the present invention, the preferred systems, apparatus, structures and methods are described herein.

It is also to be understood that, although the present invention is described and illustrated in connection with musculoskeletal stabilization systems for stabilizing spine and pelvic bone structures presenting with a dysfunction; particularly, sacroiliac (SI) joints, the invention is not limited to such procedures. According to the invention, the systems, apparatus and methods of the invention can also be readily employed to stabilize, fixate, and/or fuse other skeletal members and structures presenting with a dysfunction, including, without limitation, skeletal structures of the legs, arms, feet, hands, and like skeletal members, and shoulder, knee, and cranial skeletal structures. The systems, apparatus and methods of the invention can also be readily employed to connect connective tissue, muscles, and ligaments to bone structures.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value"

and possible ranges between values are also disclosed, as appropriately understood by the skilled artisan. For example, if the value "10" is disclosed then "less than or equal to 10" as well as "greater than or equal to 10" is also disclosed.

Definitions

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The term "dysfunctional" as used herein, means and includes a physiological abnormality, disorder, or impairment of a musculoskeletal structure, including, but limited to, skeletal members, i.e., bones, such the sacrum, ilium, and vertebrae members; and bone structures, such as SI joints and vertebrae joints; and muscles, nerves, tendons, and ligaments associated therewith.

The terms "fusion" and "arthrodesis" are used interchangeably herein in connection with bone structures, and mean and include partial or complete immobilization of adjacent bone structures, such as the sacrum and ilium bone structures.

The term "stabilization", as used herein, means and includes reinforcing, e.g., supporting, or modulating motion of adjacent articular bone structures. The term "stabilization", thus, in some instances, means and includes fusion and arthrodesis of adjacent bone structures.

The term "biodegradable", as used herein, means the ability of a structure or material thereof to breakdown and be absorbed within the body, i.e., in vivo, by one or more physical, chemical, or cellular processes.

Biodegradable polymers, according to the invention, thus include, without limitation, polylactide polymers (PLA), copolymers of lactic and glycolic acids, including poly (lactic-co-glycolic) acid (PLGA) and poly($\varepsilon$-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly (polyol sebacate) (PPS), poly(xylitol sebacate) (PXS), poly (xylitol glutamate sebacate) (PXGS), hydroxybutyrate-hydroxyvalerate copolymers, polyesters such as, but not limited to, aspartic acid and different aliphatic diols; poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly($\gamma$-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and Octyl-Seal); poly(ethylene glycol) (PEG) based compositions, including FocalSeal®, Progel™, Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly (ethylene glycol) (PGS-PEG); and/or composites thereof, e.g., PGS-hydroxyapatite (HA) composites and PGS-poly ($\varepsilon$-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of musculoskeletal structures, e.g., osseous tissue, cartilage, and connective tissue, such as tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)), and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF- 2; basic fibroblast growth factor (bFGF) (also referred to as FGF2), transforming growth factor-$\beta$ (TGF-$\beta$), including, TGF-$\beta$1 and TGF-$\beta$2; a growth hormone (GH), parathyroid hormone (PTH, including PTH1-34), transforming growth factor-$\alpha$ (TGF-$\alpha$), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2), and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs), and embryonic stem cells.

The terms "biologically active agent" and "biologically active composition" also mean and include an "extracellular vesicle (EV)", "exosome", "microsome", or "microvesicle", which are used interchangeably herein, and mean and include a biological structure formed from a hydrocarbon monolayer or bilayer configured to contain or encase a composition of matter.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-$\alpha$) inhibitors, including etanercept and infliximab; disease-modifying anti-rheumatic drugs (DMARDs), including methotrexate and hydroxychloroquine; antibiotics, anti-viral agents, steroidal anti-inflammatories, non-steroidal anti-inflammatories, anti-thrombotic agents, including anti-coagulants and anti-platelet agents; and vasodilating agents.

The terms "pharmacological agent" and "active agent" further mean and include, without limitation, the following bisphosphonate agents and compositions comprising same: risedronate (Actonel®), alendronate (Fosamax®), ibandronate (Boniva®), zoledronic acid (Reclast®), pamidronate (Aredia®), and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin, and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac, and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molybdenum particles, lead particles, and mixtures thereof.

As indicated above, the term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to systems and apparatus, and methods employing same to stabilize dysfunctional bone structures; particularly, dysfunctional spine and pelvic bone structures.

As also indicated above, although the present invention is described and illustrated in connection with stabilizing spine and pelvic bone structures (one or both of which presenting with a dysfunction), the invention is not limited to such procedures. Indeed, according to the invention, the systems, apparatus and methods of the invention can also be readily employed to stabilize, fixate, and/or fuse other skeletal members and bone structures presenting with a dysfunction, including, without limitation, the sacrum, ilium, and vertebral skeletal structures, and SI joint, shoulder, and knee bone structures.

As also indicated above and discussed in detail below, in one preferred embodiment, the musculoskeletal stabilization systems comprise a spine structure stabilization sub-system and a pelvic structure stabilization sub-system.

Spine Structure Stabilization Sub-Systems

According to the invention, spine structure stabilization sub-systems of the invention can comprise various conventional spine fixation systems, including, by way of example, the spine fixation systems disclosed in U.S. Pat. Nos. 5,545,165, 5,628,740, 5,725,527, 5,879,350, 6,050,997, 6,371,957, 6,613,050, and 7,678,136, which are incorporated by reference herein in their entirety.

In some embodiments of the invention, the spine structure stabilization sub-systems comprise a spine fixation system disclosed in U.S. Pat. Nos. 5,628,740, 6,050,997, or 7,678,136.

In one preferred embodiment, the spine structure stabilization sub-system preferably comprises the spine fixation system disclosed in U.S. Pat. No. 7,678,136.

Figure 3A:
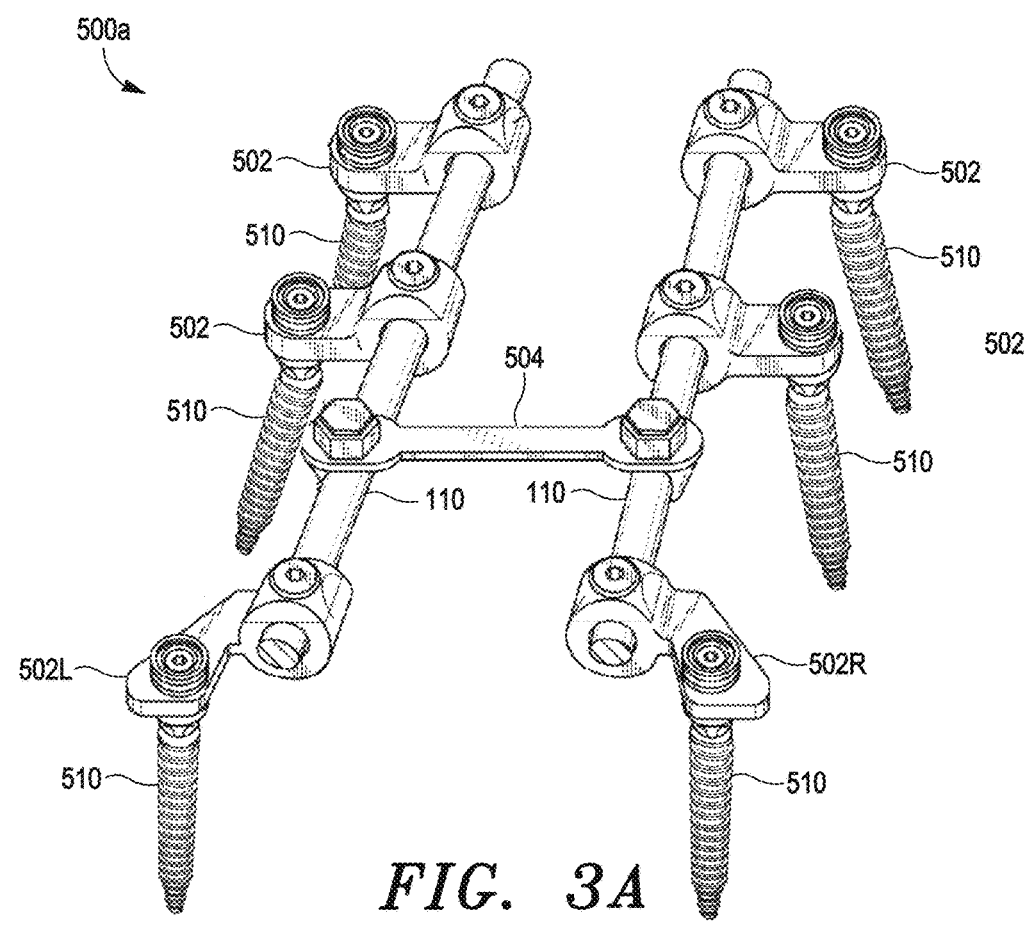
FIG. 3A is a perspective view of a spine structure stabilization sub-system, in accordance with the invention.
Figure 3B:
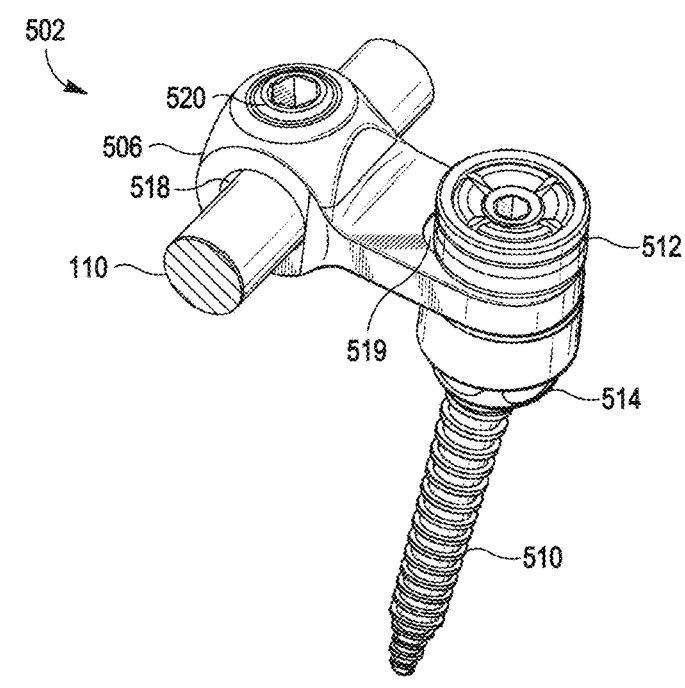
FIG. 3B is a partial perspective view of the spine structure stabilization sub-system shown in FIG. 3A, in accordance with the invention.
Figure 3C:
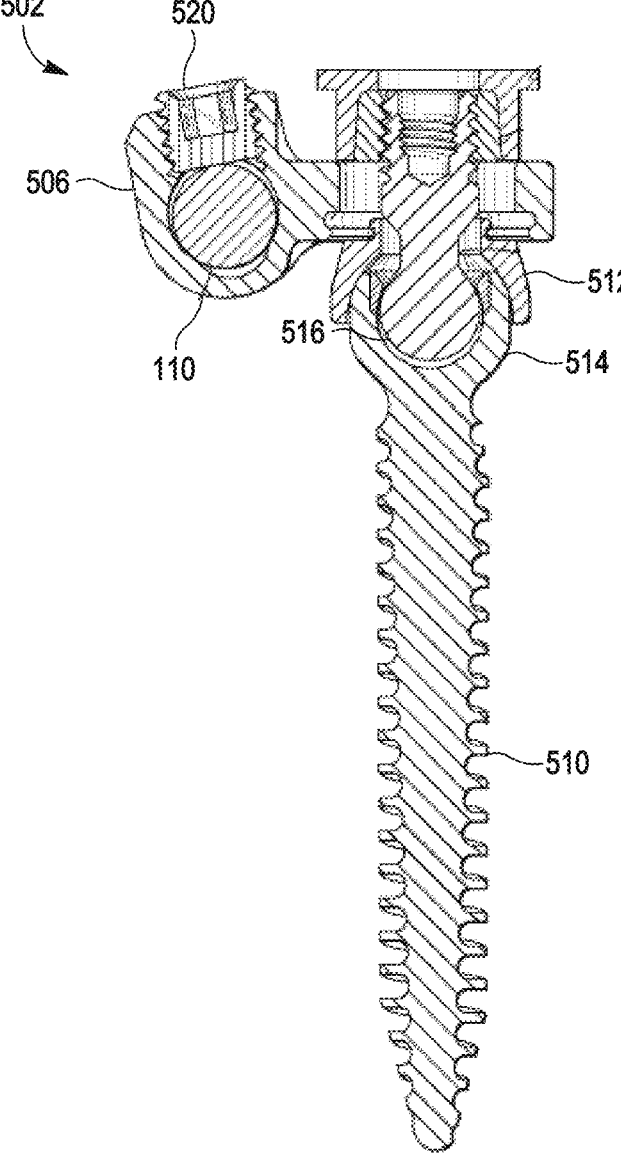
FIG. 3C is a sectional front view of the bone-engaging anchoring assembly of the spine structure stabilization sub-system shown in FIG. 3B, in accordance with the invention.
Figure 3D:
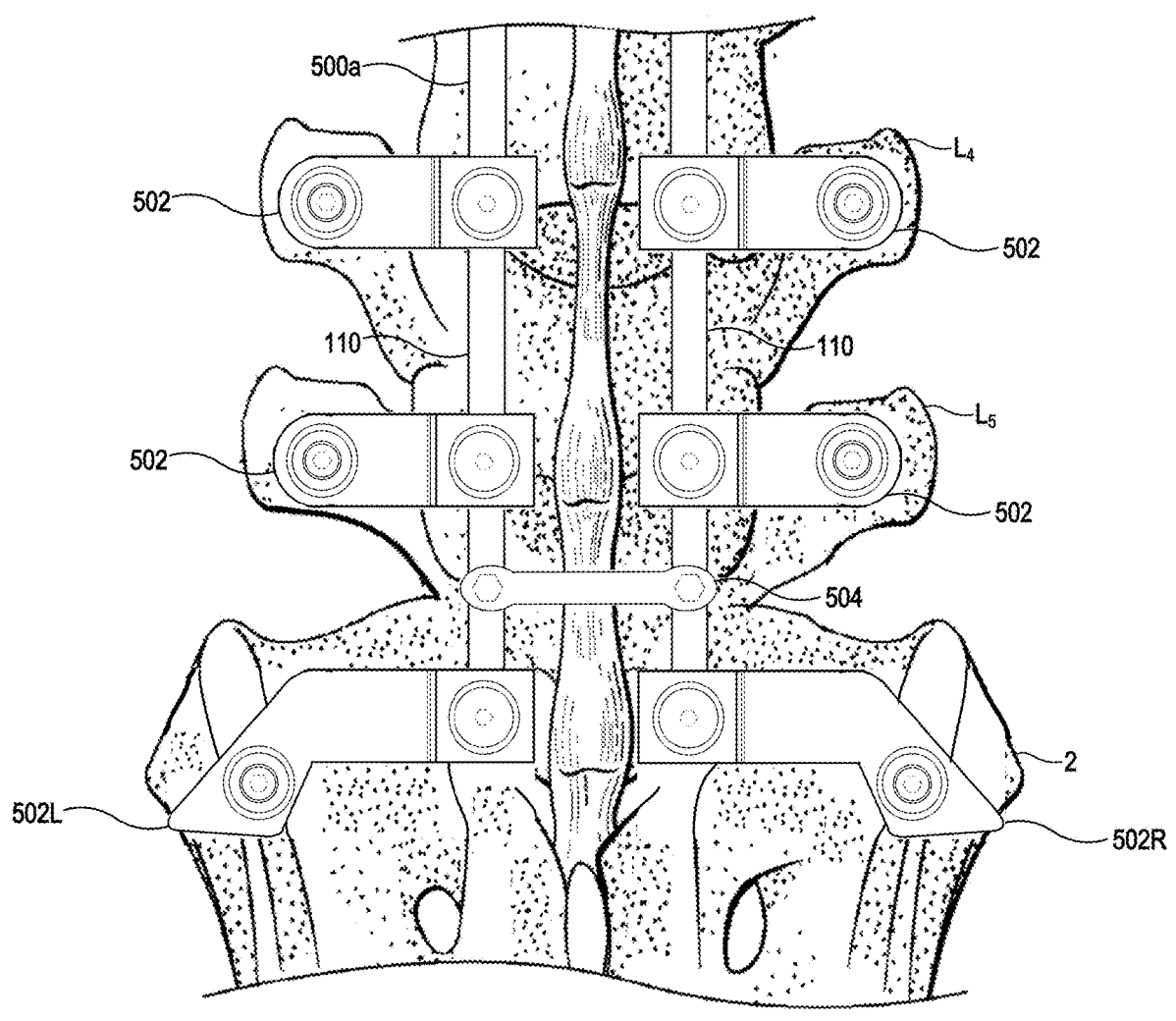
FIG. 3D is an illustration of the spine structure stabilization sub-system shown in FIG. 3A engaged to spine bone structures, in accordance with the invention.

As illustrated in FIGS. 3A-3D and described in detail in U.S. Pat. No. 7,678,136 (referred to hereinafter as "the '136 patent"), the spine fixation system, now spine structure stabilization sub-system 500a, generally comprises a pair of elongate stabilizing rods 110; each stabilizing rod 110 adapted to be positioned on opposite sides of a subject's sagittal plane, as illustrated in FIG. 3D.

As is well known in the art, the elongate stabilizing rods 110 of the spine fixation system disclosed in the '136 patent, and most other conventional spine fixation systems comprise stainless steel or titanium (Ti).

However, in some embodiments of the invention, discussed below, the spine structure stabilization sub-system based on the spine fixation system disclosed in the '136 patent comprises shape memory alloy elongate stabilizing rods 110.

In a preferred embodiment, the shape memory alloy comprises a Ni—Ti shape memory alloy, referred to hereinafter as Nitinol®.

As illustrated in FIG. 3A, the stabilizing rods 110 are interconnected by a plurality of bone-engaging anchoring assemblies 502 (which include offset bone-engaging anchoring assemblies 502L, 502R), and at least one transverse interconnector member 504.

As further illustrated in FIGS. 3A and 3B, each bone-engaging anchoring assembly 502 comprises a securement member 506 comprising a securement member lumen 518 that is configured and adapted to slidably receive the stabilizing rod 110 therein.

As additionally illustrated in FIGS. 3A and 3B, the securement member 506 further comprises a fastener assembly 520 that is adapted to secure the stabilizing rod 110 to the securement member 506.

As further illustrated in FIG. 3B, the bone-engaging anchoring assemblies 502 further comprise a bone-engaging anchoring assembly lumen 519 that is sized and configured to receive a bone screw 510 therein.

As set forth in detail in the '136 patent and illustrated in FIGS. 3B and 3D, the bone screws 510 are configured to engage vertebral bone structures, whereby spine structure stabilization sub-system 500a is engaged thereto.

As set forth in detail in the '136 patent and partially illustrated in FIGS. 3B and 3C, the bone screw 510 comprises a poly-axial or multi-axial head region 512 that is adapted and configured to allow versatile angulation of the head region 512 to accommodate a multitude of configurations, positions, and trajectories of the stabilizing rods 110.

As illustrated in FIG. 3C, the head region 512 comprises a rounded engagement head 516 that pivotally mounts within a corresponding rounded retaining socket 514 of the bone screw 510 to allow for poly-axial adjustment of the bone screw 510 relative to the head region 512.

Further details of the spine structure stabilization sub-system 500a are set forth in the '136 patent, which, as indicated above, is incorporated by reference herein in its entirety.

Pelvic Structure Stabilization Sub-Systems

As indicated above, in a preferred embodiment, the pelvic structure stabilization sub-systems of the invention comprise first and second prosthesis systems; the first prosthesis system comprising a first prosthesis and the second prosthesis system comprising a second prosthesis.

As discussed in detail below, in a preferred embodiment of the invention, the first and second prostheses comprise spine structure stabilization sub-system engagement means configured and adapted to engage (and cooperate with) a spine structure stabilization sub-system of the invention.

In a preferred embodiment, the first and second prostheses are also configured and adapted to be delivered to a SI joint via a posterior trajectory.

As indicated above, SI joint stabilization, including minimally-invasive SI joint stabilization, typically comprises surgical placement of a joint prosthesis proximate to or in a SI joint via anterior, lateral and posterior approaches to the SI joint.

Figure 2A:
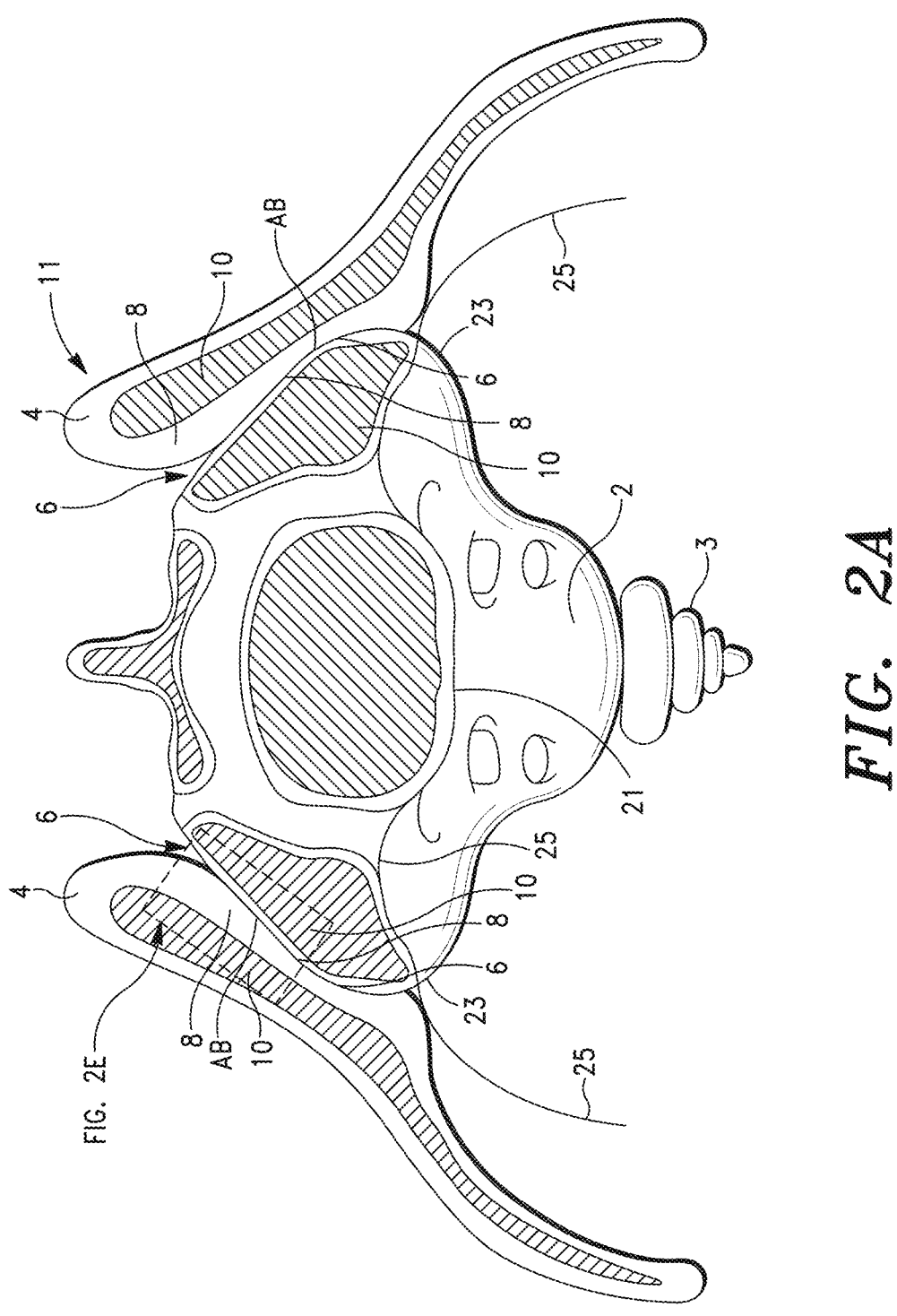
FIG. 2A is a schematic illustration of a human pelvic region from an anteroposterior (AP) perspective showing the SI joints thereof.
Figure 2B:
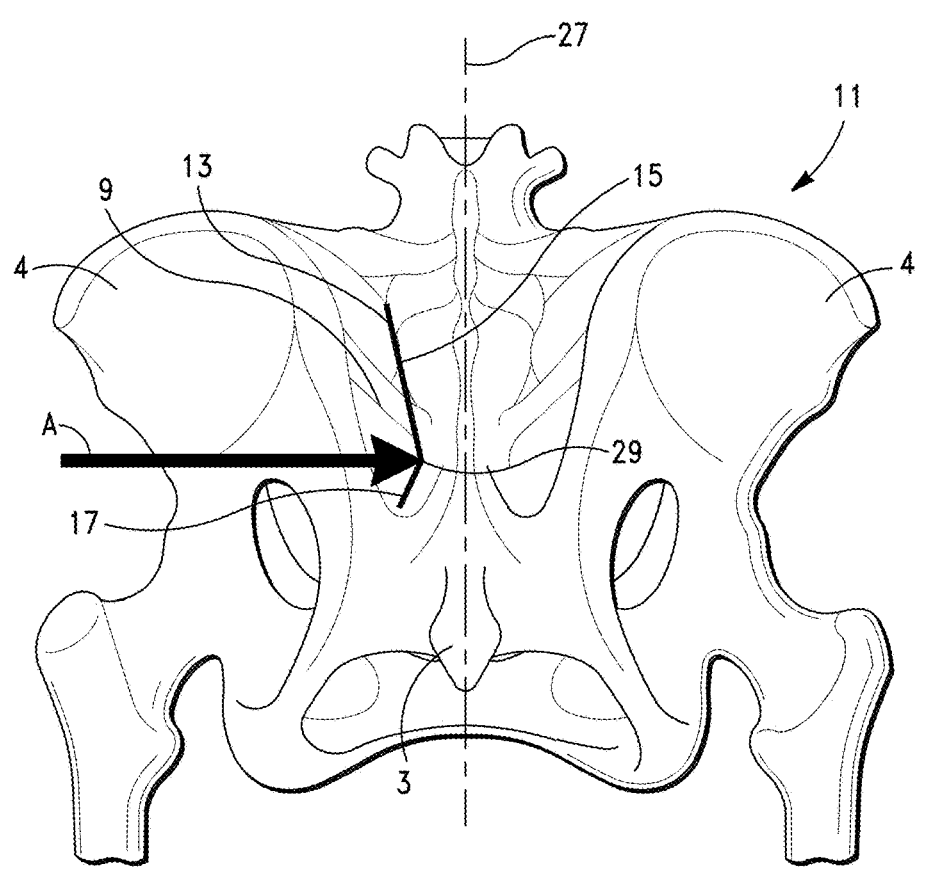
FIG. 2B is another schematic illustration of a human pelvic region from a posterior perspective showing the adjoining sacrum and ilium bone structures, and ligamentous structures thereof.
Figure 2C:
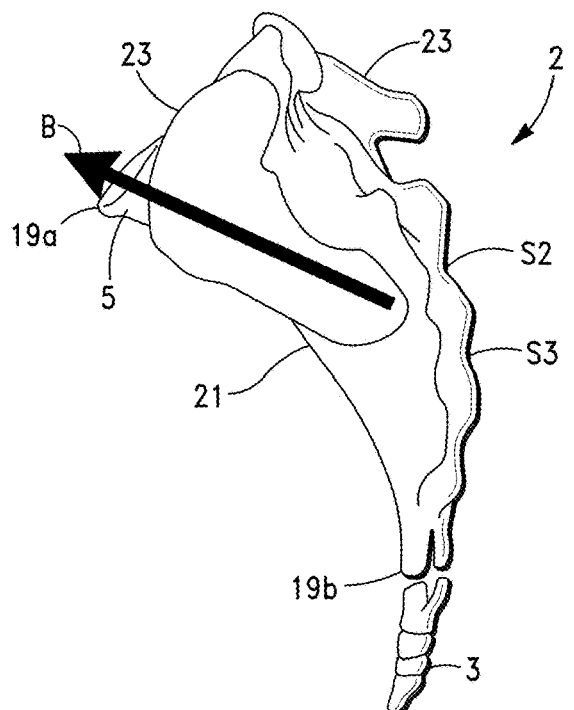
FIG. 2C is a schematic illustration of the sacrum and coccyx from a lateral perspective showing the sacral promontory and the articular surface of sacrum.
Figure 2D:
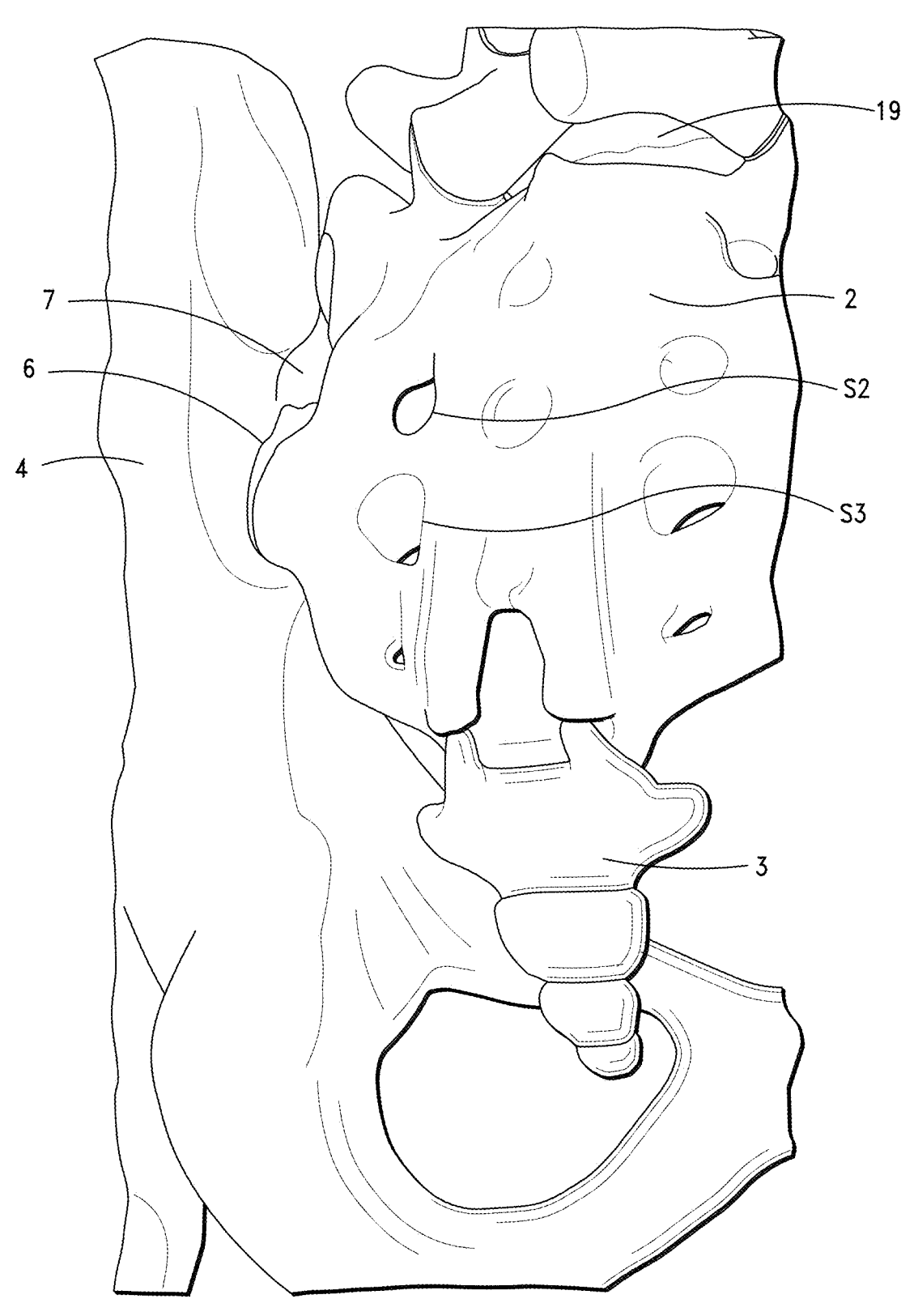
FIG. 2D is another schematic illustration of a human pelvic region from a posterior inferior perspective showing the adjoining sacrum and ilium bone structures of an SI joint, and an SI joint dorsal recess between the sacrum and ilium bone structures.

From the perspective of FIG. 2A, an anterior approach to the SI joint 6 would be substantially perpendicular to the page upon which FIG. 2A is printed.

Figure 2E:
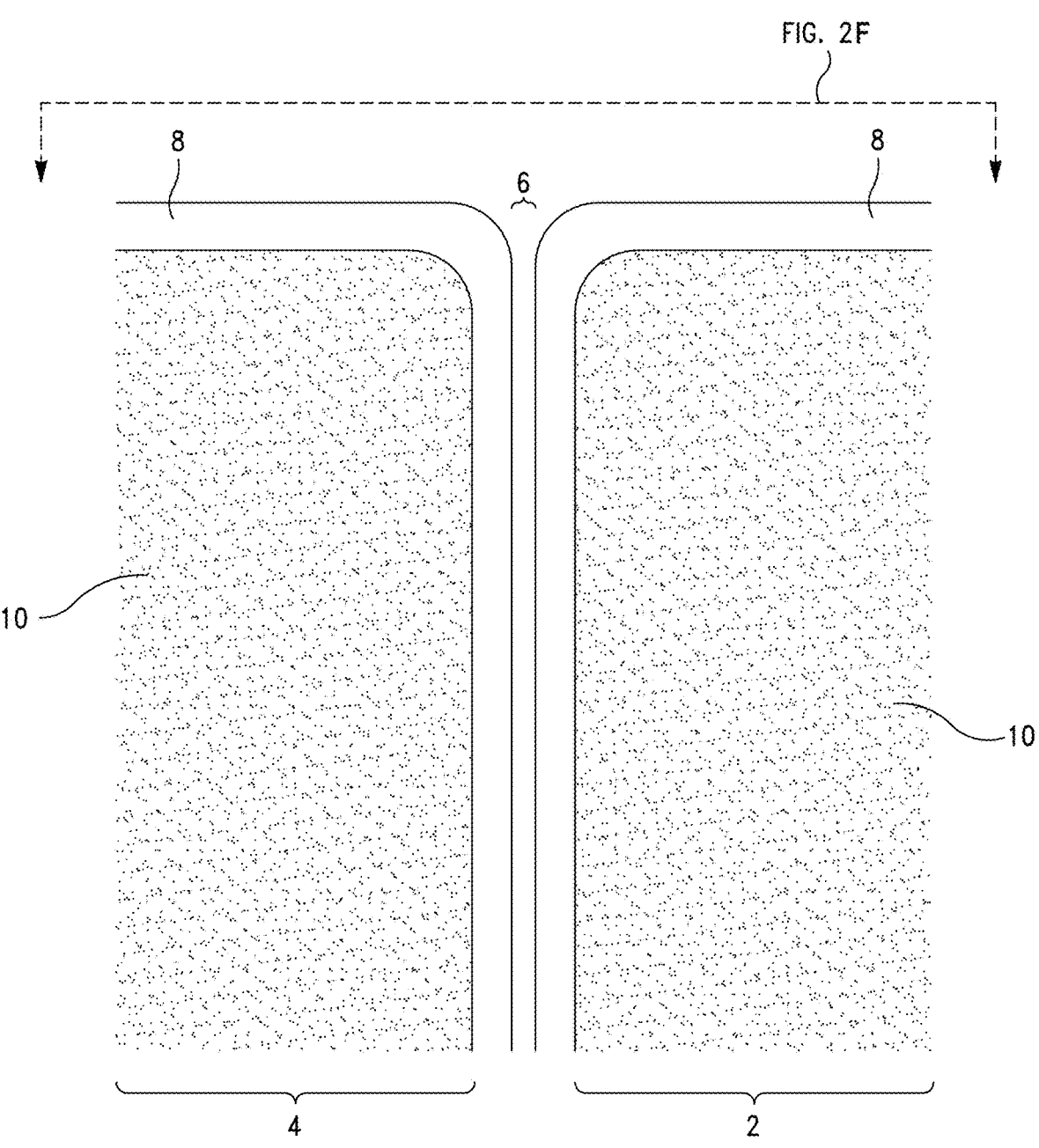
FIG. 2E is an illustration of a SI joint from a superior perspective showing the adjoining sacrum and ilium articular surfaces.

Referring now to FIG. 2E there is shown an illustration of a SI joint 6 and surrounding structures. For illustrative simplicity, a uniform layer of cortical bone 8 is shown adjacent a deeper layer of trabecular bone 10 on both of the depicted sacrum 2 and ilium 4 structures. However, in actuality, such layers are far less uniform and homogeneous.

Figure 2F:
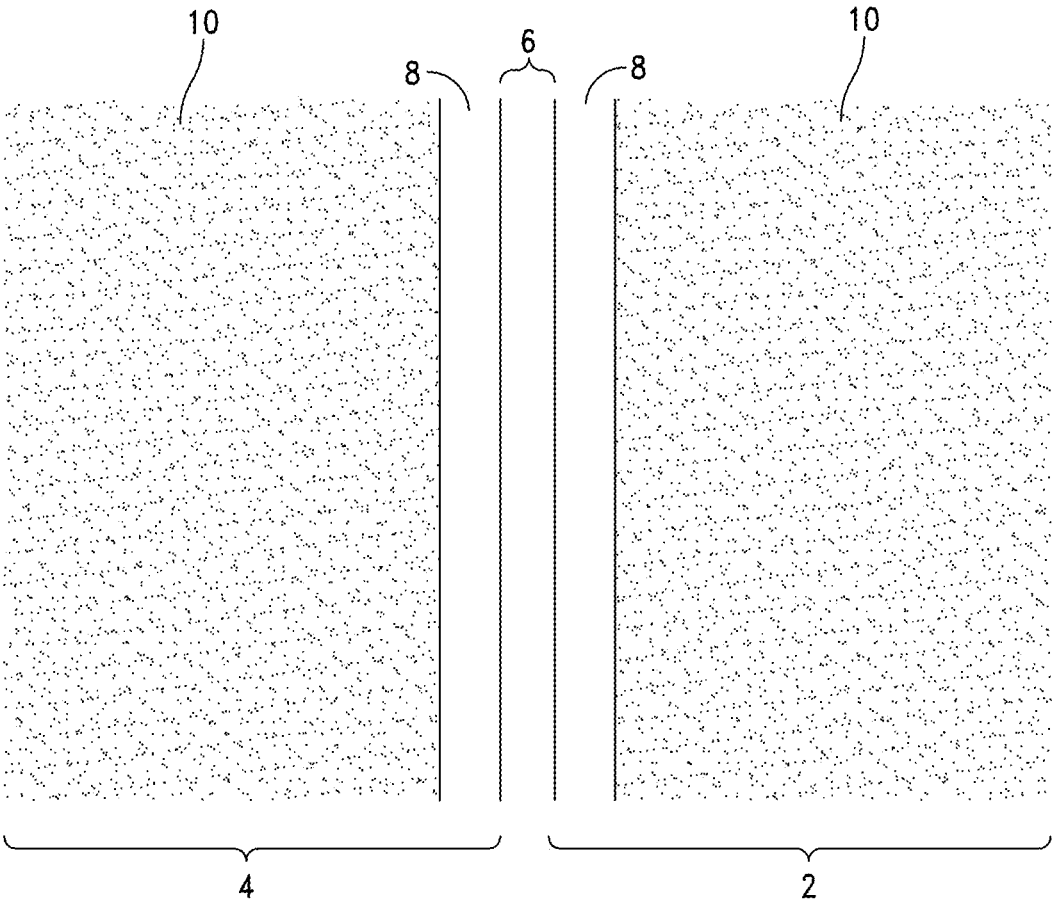
FIG. 2F is another illustration of a SI joint from a posterior perspective showing the adjoining sacrum and ilium articular surfaces.
Figure 2G:
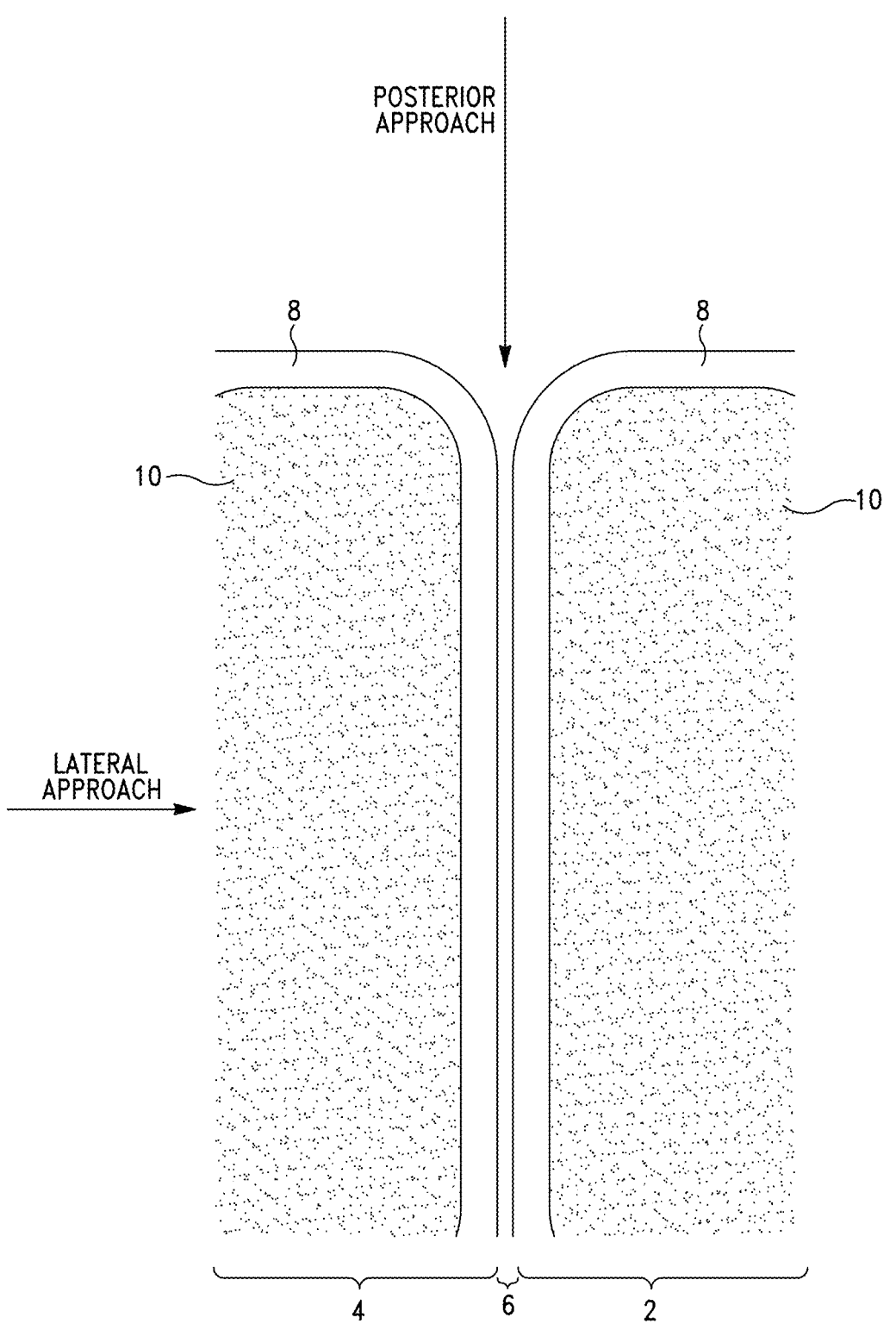
FIG. 2G is a further illustration of the SI joint shown in FIG. 2F showing lateral and posterior approaches to the SI joint, in accordance with the invention.

Referring now to FIG. 2F, there is shown a view of the same structure from a different posterior perspective. From the perspective of FIG. 2F, a posterior approach to the SI joint 6 would be substantially perpendicular to the page upon which FIG. 2F is printed. Indeed, referring to FIG. 2G, a variation similar to that depicted in FIG. 2E is illustrated, showing an approximate approach vector for a lateral approach to the SI joint 6 versus a posterior approach, using the orientation paradigms introduced in FIGS. 2A and 2F-2G.

As indicated above, a major disadvantage associated with many conventional anterior or lateral approaches to a SI joint is that muscles and ligaments are typically disrupted and often damaged. Nerves and blood vessels are also susceptible to damage during such SI joint stabilization methods.

In contrast, posterior delivery of joint prostheses of the invention to a SI joint is much less invasive. Indeed, less tissue and fewer muscles are disrupted, and nerves and large blood vessels are avoided.

Thus, as indicated above, in a preferred embodiment, the first and second prostheses of the first and second prosthesis systems and, hence, pelvic structure stabilization sub-systems of the invention are configured and adapted to be delivered to SI joints via a posterior approach.

According to the invention, suitable first and second prostheses for placement in SI joints, and, in some embodiments, placement in spinal bone structures, are disclosed in Applicant's U.S. Pat. Nos. 9,492,284, 11,147,675, and 11,273,042 and Co-Pending U.S. application Ser. Nos. 17/463,779, 17/740,568, 17/749,199, 17/833,987, 17/833,098, and 17/833,960, which are incorporated by reference herein in their entirety.

In a preferred embodiment, the first and second prostheses comprise the prosthesis denoted "prosthesis 70" in Applicant's Co-Pending U.S. application Ser. Nos. 17/469,132, 17/468,811, 17/463,831, and 17/834,392.

Figures 4A, 4B:
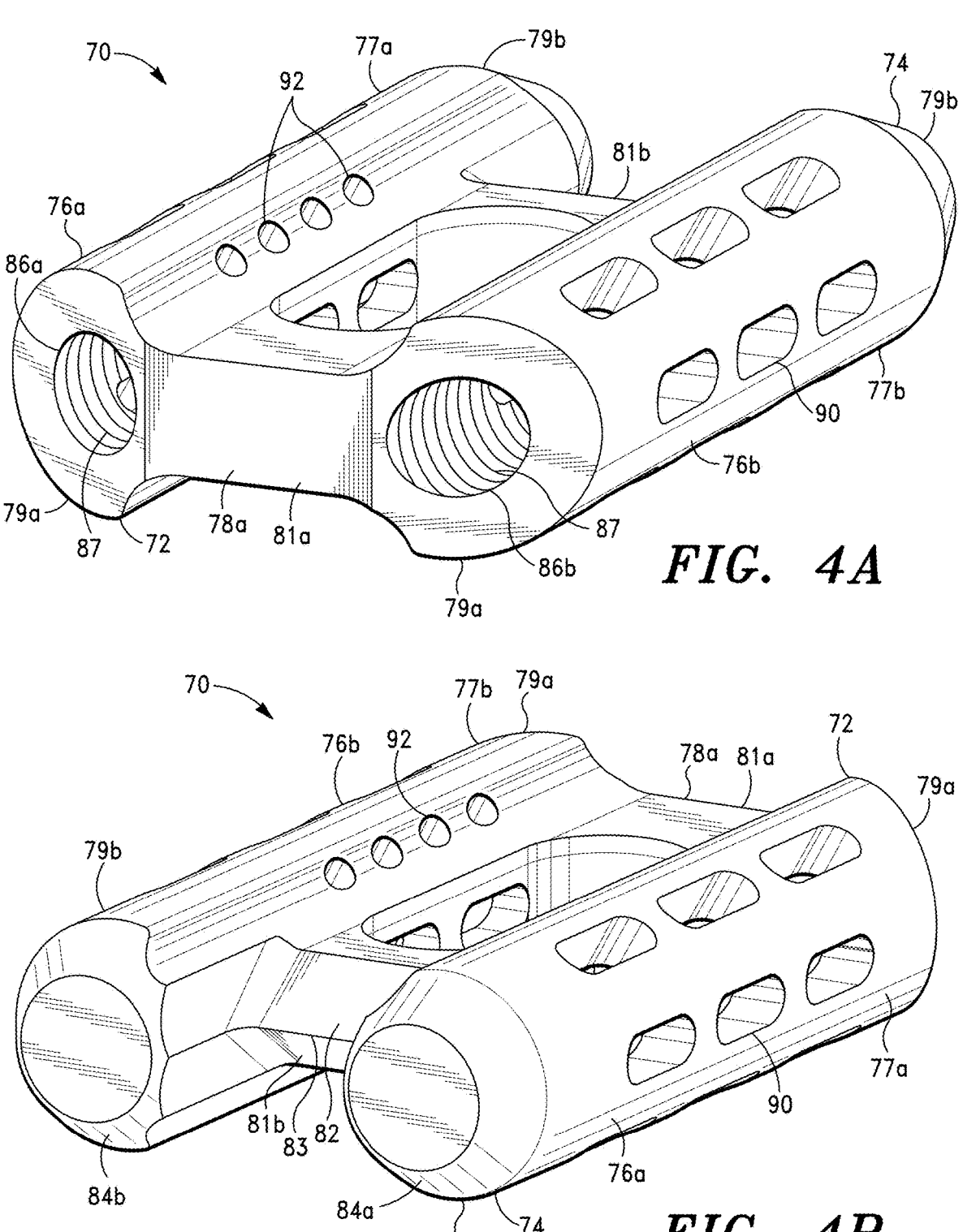
FIG. 4A is a perspective view of one embodiment of a pelvic structure stabilization sub-system prosthesis, in accordance with the invention.
FIG. 4B is further perspective view of the prosthesis shown in FIG. 4A, in accordance with the invention.

As illustrated in FIGS. 4A and 4B, the prosthesis 70 comprises a biocompatible and, hence, implantable member comprising proximal and distal ends 72, 74, and first and second elongated partially cylindrical sections 76a, 76b connected to a bridge section 78a, whereby the prosthesis 70 comprises a continuous exterior surface comprising first and second partially cylindrical surface regions 77a, 77b.

As further illustrated in FIGS. 4A and 4B, the first and second partially cylindrical sections 76a, 76b comprise proximal and distal ends 79a, 79b. The bridge section 78a similarly comprises proximal and distal ends 81a, 81b.

As further illustrated in FIGS. 4A and 4B, the first partially cylindrical surface region 77a preferably comprises a partially cylindrical surface region shape that corresponds to at least a first portion of a pilot opening in a bone structure, in this instance, a SI joint, and the second partially cylindrical surface region 77b similarly preferably comprises a partially cylindrical surface region shape that corresponds to at least a second portion of the pilot opening in the bone structure.

As illustrated in FIG. 4B, the distal end 81b of the bridge section 78a preferably comprises a taper region 82, which is configured and adapted to disrupt, i.e., cut into and through, articular cartilage and cortical bone 8 (and, in some aspects, trabecular bone 10), which define a SI joint.

As further illustrated in FIG. 4B, the distal ends 79b of the first and second elongated partially cylindrical sections 76a, 76b also preferably comprise tapered regions 84a, 84b, which facilitate insertion of the distal ends 79b of the first and second elongated partially cylindrical sections 76a, 76b into pilot openings in bone structures.

Figure 4C:
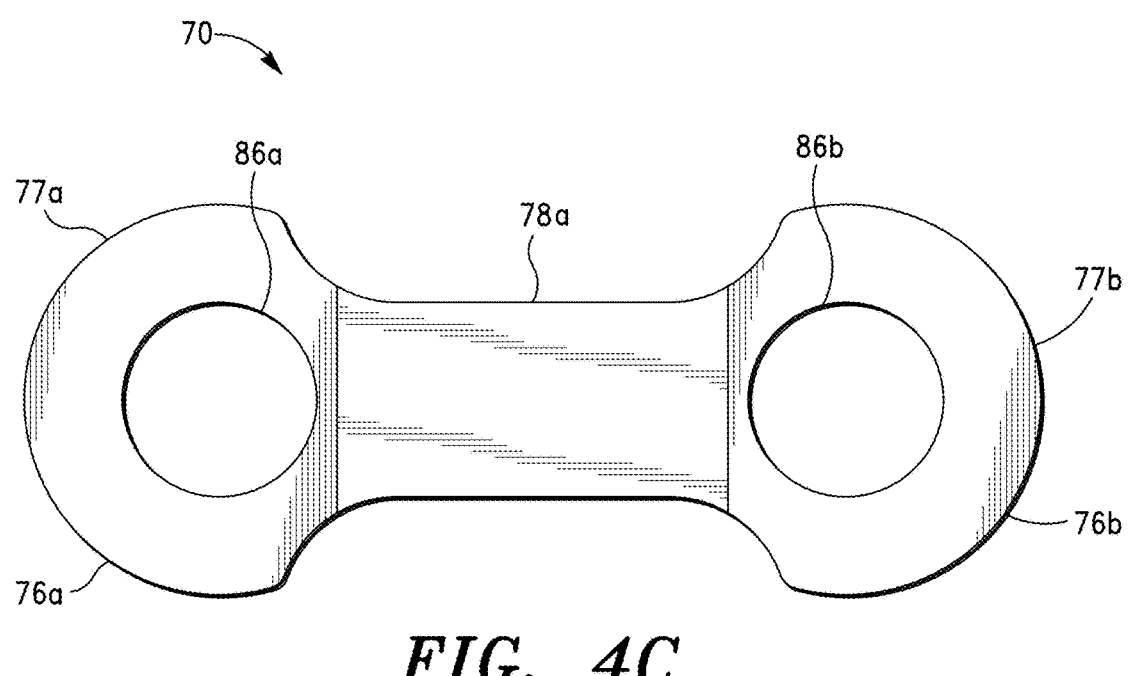
FIG. 4C is a rear plan view of the prosthesis shown in FIG. 4A, in accordance with the invention.
Figure 4D:
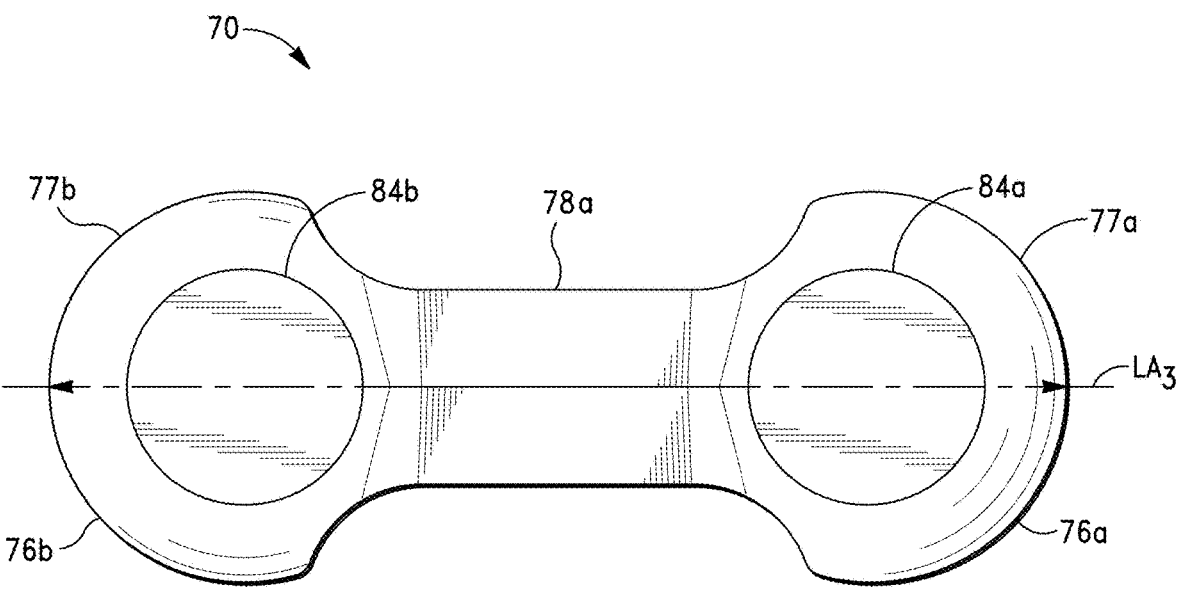
FIG. 4D is a front plan view of the prosthesis shown in FIG. 4A, in accordance with the invention.

As illustrated in FIGS. 4C and 4F, the first elongated partially cylindrical section 76a of the joint prosthesis 70 comprises an internal prosthesis engagement member lumen 86a that extends from the proximal end 79a of the first elongated partially cylindrical section 76a.

As illustrated in FIGS. 4A and 4C, the second elongated partially cylindrical section 76b of the joint prosthesis 70 also comprises an internal prosthesis engagement member lumen 86b that extends from the proximal end 79a of the second elongated partially cylindrical section 76b.

As further illustrated in FIG. 4A, in a preferred embodiment of the invention, the internal prosthesis engagement member lumens 86a, 86b of the first and second elongated partially cylindrical sections 76a, 76b comprise internal threaded regions 87 adapted to engage a prosthesis deployment assembly adapted to deliver the prosthesis 70 to bone structure, in this instance, a SI joint, such as set forth in Co-pending U.S. application Ser. No. 17/463,831, and, as discussed below, spine stabilization sub-system engagement means.

In a preferred embodiment, the internal prosthesis engagement lumens 86a, 86b are also configured to receive agents and compositions that further facilitate adhesion of the prosthesis 70 to and in bone structures. Such agents and compositions are set forth in in Co-pending U.S. application Ser. No. 17/463,831.

In a preferred embodiment, the internal prosthesis engagement lumens 86a, 86b are also configured to receive the aforementioned biologically active agents and compositions, including osteogenic agents and compositions, and pharmacological agents and compositions that promote or induce proliferation, and/or growth and/or remodeling and/or regeneration of osseous tissue of a dysfunctional joint and/or facilitate osseous tissue ingrowth into the prosthesis 70 when the prosthesis 70 is disposed in a bone structure, such as an SI joint.

Referring back to FIGS. 4A and 4B, in a preferred embodiment, the prosthesis 70 further comprises a plurality of slots 90 and apertures 92, which preferably are in communication with the internal prosthesis engagement member lumens 86a, 86b.

In a preferred embodiment, the slots and apertures are sized and configured to allow the adhesive compositions and/or biologically active agent compositions and/or pharmacological agent compositions to be dispersed out of the internal prosthesis engagement member lumens 86a, 86b and delivered to bone structures when the prosthesis 70 is disposed therein.

As set forth in Co-pending U.S. application Ser. No. 17/469,132, the prosthesis 70 can comprise various biocompatible materials, including metals and metal alloys, such as titanium, stainless-steel, cobalt-chromium alloys and nickel-titanium alloys (including Nitinol®), and various biocompatible polymers, including, without limitation, reinforced polymers, such as carbon fiber reinforced polymers and metal-framed polymers.

According to the invention, the prosthesis can comprise various sizes to accommodate placement in various bone structures, e.g., SI joints, vertebrae, etc.

The prosthesis 70 can additionally comprise a porous structure to facilitate (i) adhesion of the prosthesis 70 to bone structures and (ii) bone or osseous tissue ingrowth into the prosthesis 70.

As further set forth in Co-pending U.S. application Ser. No. 17/469,132, the prosthesis 70 can further comprise an outer coating.

According to the invention, the outer coating can comprise one of the aforementioned osteogenic compositions, one of the aforementioned biologically active agent compositions, or one of the aforementioned pharmacological agent compositions.

According to the invention, the outer coating can further comprise a biocompatible adhesive composition, such as, without limitation, poly(L-glutamic acid)-based compositions, poly(γ-glutamic acid)-based compositions, poly(alkyl cyano acrylate)-based compositions, and polyacrylic acid-based compositions.

In some embodiments, the outer coating comprises one of the aforementioned polymers and/or compositions comprising same.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites, and compositions comprising same.

As set forth in Applicant's Co-Pending U.S. application Ser. No. 17/469,132, PGS and derivatives thereof possess a unique property of inducing remodeling of damaged osseous or bone tissue and, hence, healing of the associated bone structures when disposed proximate thereto.

A further seminal property of PGS is that its physical state can be modulated during synthesis by controlling the "degree of esterification" via at least one crosslinking agent, e.g., methylene diphenyl diisocyanate (MDI), whereby the PGS exhibits adhesive properties.

As further set forth in Co-pending U.S. application Ser. No. 17/469,132, PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS outer coatings and PGS and PGSA based compositions further comprise one or more of the aforementioned biologically active or pharmacological agents.

As indicated above, in a preferred embodiment of the invention, prosthesis 70 (i.e., the first and second prostheses of the pelvic structure stabilization sub-system) further comprises spine structure stabilization sub-system engagement means configured and adapted to engage (and cooperate with) a spine structure stabilization sub-system of the invention and, in particular, spine structure stabilization sub-system 500a.

As discussed in detail below, in a preferred embodiment, the spine structure stabilization sub-system engagement means are adapted to threadably engage at least the first internal threads of the first elongated partially cylindrical section of prosthesis 70 and the spine structure stabilization sub-system.

As further discussed below, in some embodiments of the invention, the spine structure stabilization sub-system engagement means is adapted to threadably engage the first internal threads of the first elongated partially cylindrical section 76a of prosthesis 70 and the second internal threads of the second elongated partially cylindrical section 76b of prosthesis 70 and the spine structure stabilization sub-system.

Figure 5B:
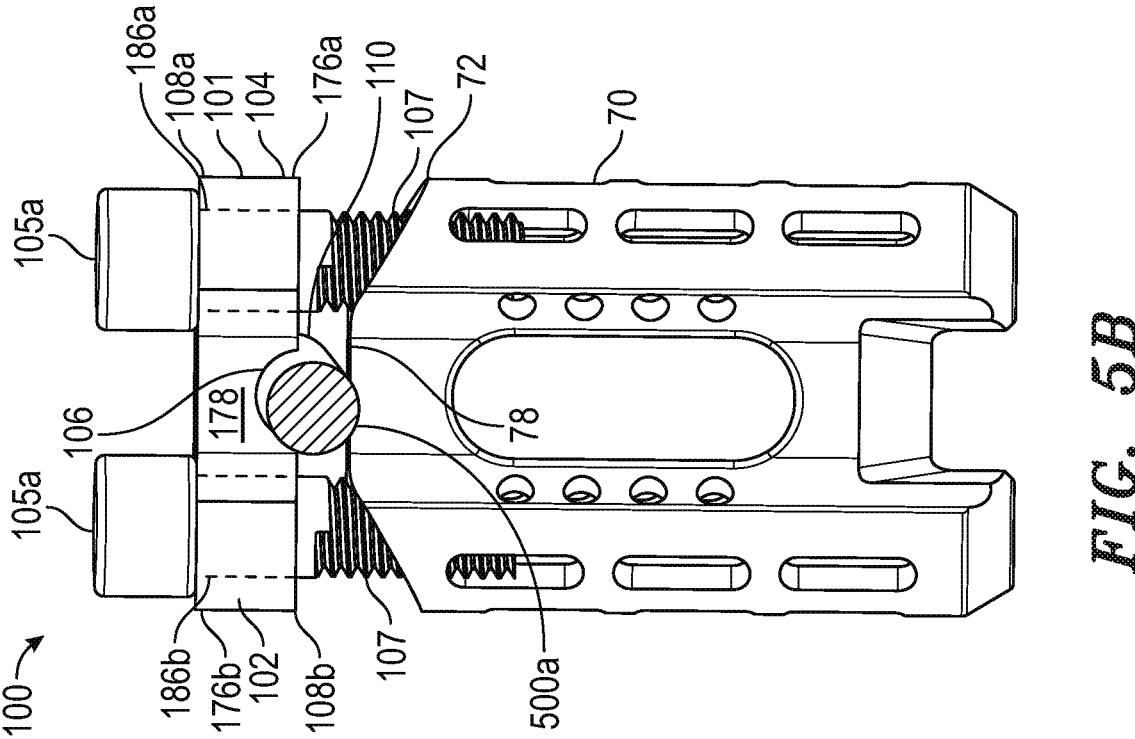
FIG. 5B is a front plan view of the pelvic structure stabilization sub-system prosthesis shown in FIG. 5A, in accordance with the invention.
Figure 5A:
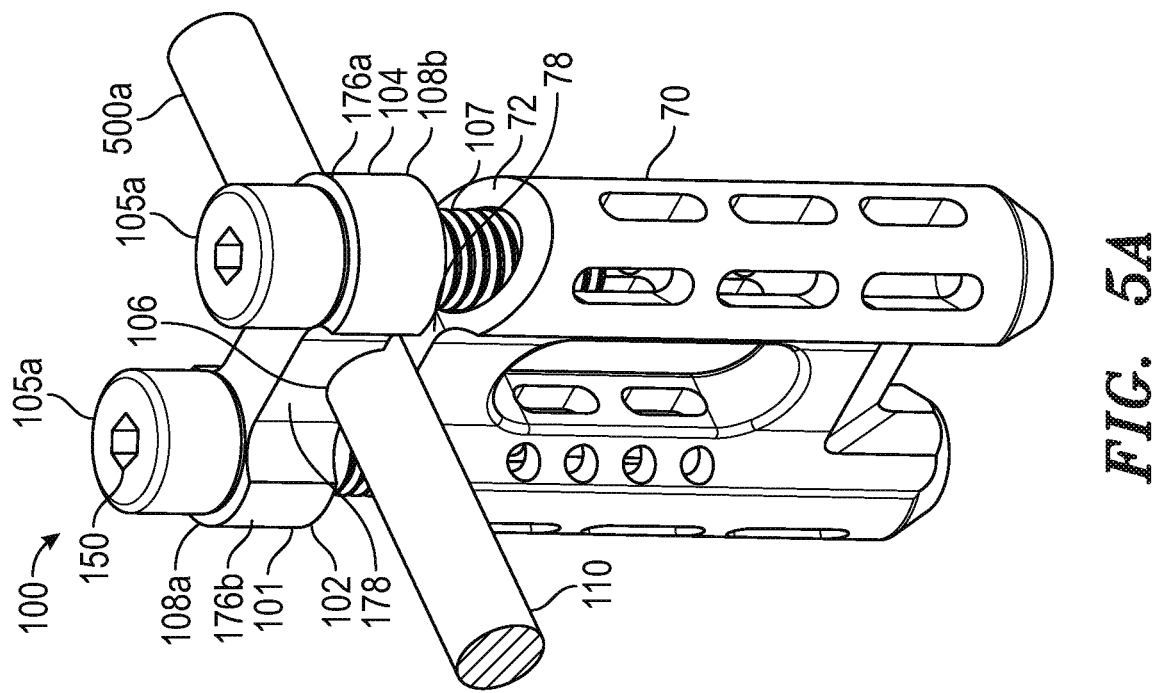
FIG. 5A is a perspective view of one embodiment of a pelvic structure stabilization sub-system prosthesis comprising one embodiment of spine structure stabilization sub-system engagement means, in accordance with the invention.

Referring now to FIGS. 5A and 5B, there is shown one embodiment of a prosthesis system of the invention, i.e., first prosthesis system and/or second prosthesis system of the invention, (denoted "100") comprising prosthesis 70 and one embodiment of spine stabilization sub-system engagement means of the invention (denoted "101"), which, as illustrated in FIGS. 5A and 5B, is adapted to engage (and cooperate with) spine structure stabilization sub-system 500a, i.e., a stabilizing bar 110 thereof.

As illustrated in FIGS. 5A and 5B, the spine stabilization sub-system engagement means 101 comprises a base member 104 comprising proximal and distal ends 108a, 108b, and first and second elongated partially cylindrical sections 176a, 176b connected to a bridge section 178.

As further illustrated in FIGS. 5A and 5B, in a preferred embodiment, the first and second elongated partially cylindrical sections 176a, 176b of the base member 104 comprise base member engagement lumens 186a, 186b that extend from the proximal end 108a to the distal end 108b of the base member 104.

As further illustrated in FIGS. 5A and 5B, the base member 104 further comprises a curved or concave region 106 on the distal end 108b that is sized and configured to mate with and seat a stabilizing rod of a spine stabilization sub-system of the invention, in this instance, stabilizing rod 110 of the spine stabilization sub-system 500a.

As additionally illustrated in FIGS. 5A and 5B, the spine stabilization sub-system engagement means 101 further comprises bolts 105a that are sized and configured to slidably translate in and through the base member engagement lumens 186a, 186b and threadably engage the internal threads 87 of the internal prosthesis engagement member lumens 86a, 86b of the first and second elongated partially cylindrical sections 76a, 76b of the prosthesis 70, whereby the spine stabilization sub-system engagement means 101 can be securely engaged to prosthesis 70.

As further illustrated in FIG. 5A, in a preferred embodiment, the bolts 105a comprise an internal insertion tool engagement region 150, which is configured to receive and cooperate with an external deployment and/or extraction tool or assembly. In some embodiments, the internal insertion tool engagement region 150 comprises a hex configuration or region, such as illustrated in FIG. 5A, which is adapted to receive and cooperate with an external "hex" (or Allen head) tool or assembly.

Figure 5D:
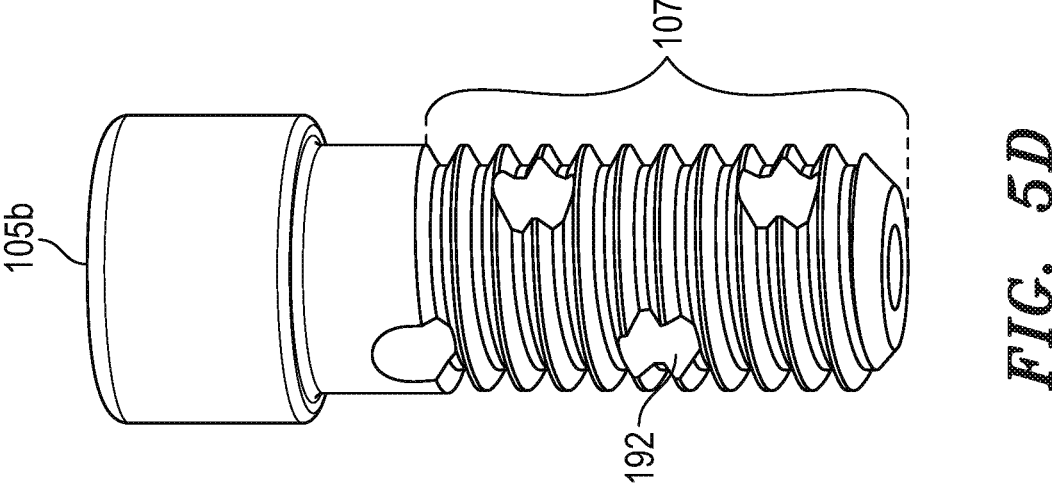
FIG. 5D is a front plan view of the spine structure stabilization sub-system engagement means bolt shown in FIG. 5C, in accordance with the invention.
Figure 5C:
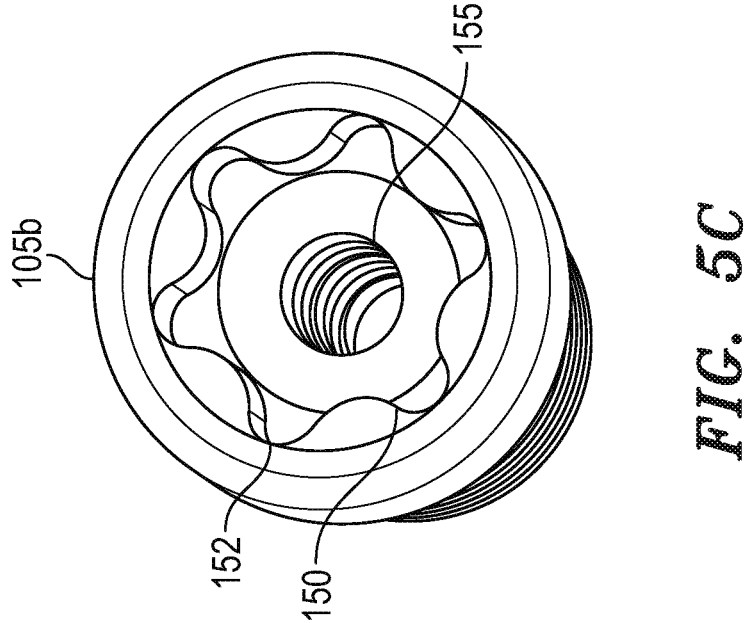
FIG. 5C is a top plan view of one embodiment of the securing means, i.e., bolt, for the spine structure stabilization sub-system engagement means shown in FIG. 5A, in accordance with the invention.

Referring now to FIGS. 5C and 5D, there is shown another embodiment of bolts 105a (now denoted "105b") that are sized and configured to slidably translate in and through the base member engagement lumens 186a, 186b and threadably engage the internal threads 87 of the internal prosthesis engagement member lumens 86a, 86b of the first and second elongated partially cylindrical sections 76a, 76b of the prosthesis 70.

As illustrated in FIG. 5C, the bolts 105b similarly comprise an internal insertion tool engagement region 150. However, in this embodiment, the internal insertion tool engagement region 150 comprises a hexa-lobe configuration or region 152, which is adapted to receive and cooperate with an external "hexa-lobal" (or Torx® head) tool or assembly.

In some embodiments, the threaded region 107 of the bolts 105b (and, in some instances, bolts 105a) further comprises an internal bolt region 155 that is sized and configured to receive agents and compositions that facilitate adhesion of the bolts 105b (and bolts 105a) to the prosthesis 70.

As illustrated in FIG. 5D, in the noted embodiments, the threaded region 107 of the bolts 105*b* (and bolts 105*a*) preferably comprises a plurality of fenestrations 192, which preferably are in communication with the internal bolt region 155.

According to the invention, when a stabilizing rod of a spine stabilization sub-system of the invention, such as stabilizing rod 110 of the spine stabilization sub-system 500*a*, is seated in the concave region 106 of the base member 104 and the bolts 105*a* or 105*b* are engaged to and translated into the internal base member engagement lumens 186*a*, 186*b* of the base member 104, the stabilizing rod, e.g. stabilizing rod 110, is secured between the concave region 106 of the base member 104 and the proximal end 81*a* of the prosthesis bridge section 78, as illustrated in FIGS. 5A and 5B.

Figure 6B:
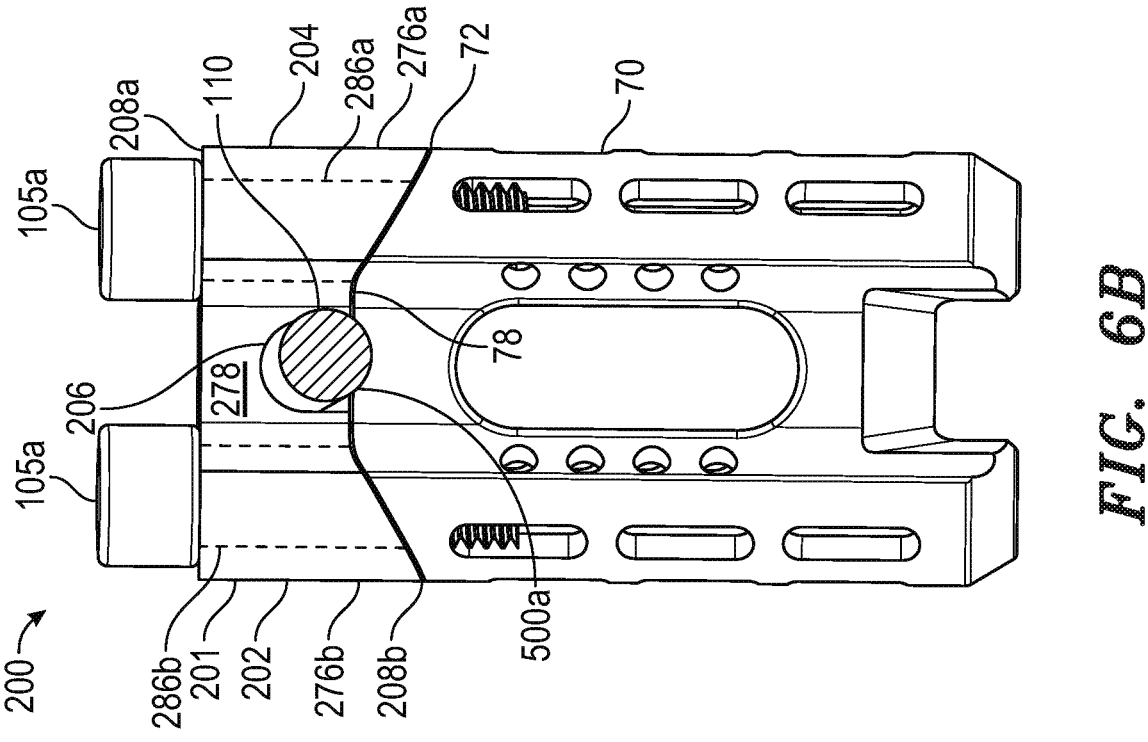
FIG. 6B is a front plan view of the pelvic structure stabilization sub-system prosthesis shown in FIG. 6A, in accordance with the invention.
Figure 6A:
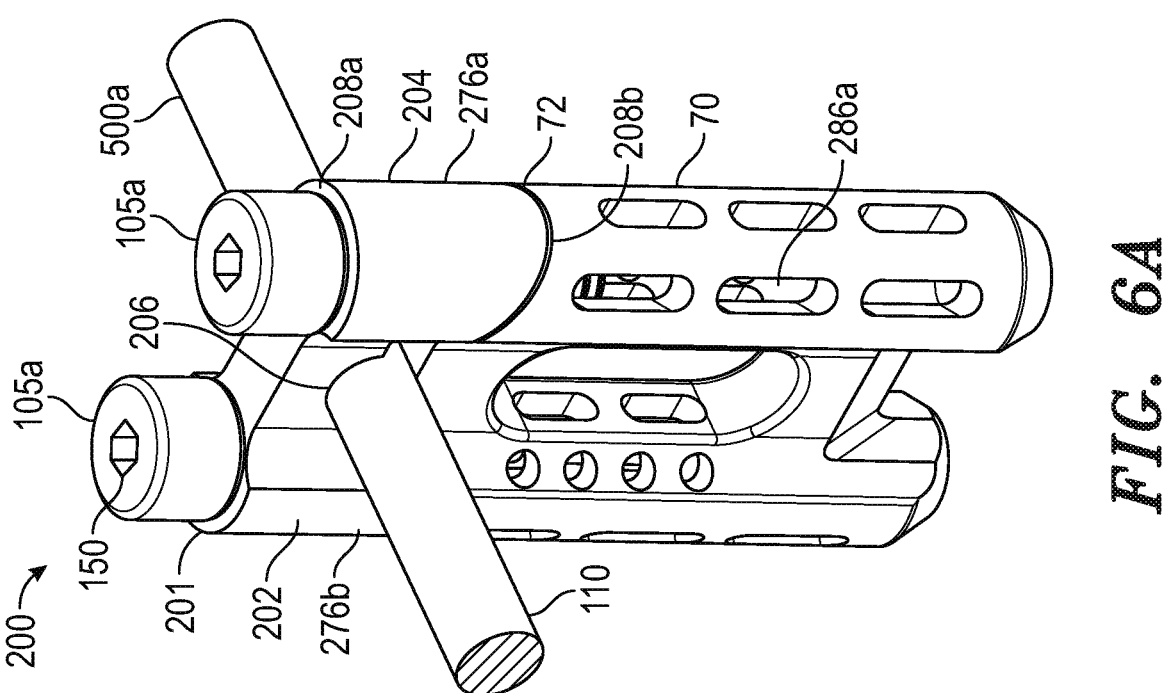
FIG. 6A is a perspective view of the pelvic structure stabilization sub-system prosthesis shown in FIG. 5A comprising another embodiment of spine structure stabilization sub-system engagement means, in accordance with the invention.

Referring now to FIGS. 6A and 6B, there is shown another embodiment of a prosthesis system of the invention, i.e., first prosthesis system and/or second prosthesis system of the invention, (denoted "200") comprising prosthesis 70 and another embodiment of spine stabilization sub-system engagement means of the invention (denoted "201"), which, as illustrated in FIGS. 6A and 6B, is similarly adapted to engage (and cooperate with) spine structure stabilization sub-system 500*a*, i.e., a stabilizing bar 110 thereof.

As illustrated in FIGS. 6A and 6B, the spine stabilization sub-system engagement means 201 similarly comprises a base member 204 comprising proximal and distal ends 208*a*, 208*b*, and first and second elongated partially cylindrical sections 276*a*, 276*b* connected to a bridge section 278.

As further illustrated in FIGS. 6A and 6B, the first and second elongated partially cylindrical sections 276*a*, 276*b* of the base member 204 similarly comprise base member engagement lumens 286*a*, 286*b* that extend from the proximal end 208*a* to the distal end 208*b* of the base member 204.

As further illustrated in FIGS. 6A and 6B, in a preferred embodiment, the distal end 208*b* of the base member 204 is sized and configured to conform to the shape of the proximal ends of the first and second elongated partially cylindrical sections 76*a*, 76*b* of prosthesis 70.

As further illustrated in FIGS. 6A and 6B, the base member 204 similarly comprises a curved or concave region 206 that is similarly sized and configured to conform to, mate with, and seat a stabilizing rod of a spine stabilization sub-system of the invention, in this instance, stabilizing rod 110 of the spine stabilization sub-system 500*a*.

As additionally illustrated in FIGS. 6A and 6B, the spine stabilization sub-system engagement means 201 further similarly comprises bolts 105*a* or 105*b* that are sized and configured to slidably translate in and through the base member engagement lumens 286*a*, 286*b* and threadably engage the internal threads 87 of the internal prosthesis engagement member lumens 86*a*, 86*b* of the first and second elongated partially cylindrical sections 76*a*, 76*b* of the prosthesis 70, whereby the spine stabilization sub-system engagement means 201 can be securely engaged to prosthesis 70.

According to the invention, when a stabilizing rod of a spine stabilization sub-system of the invention, such as stabilizing rod 110 of the spine stabilization sub-system 500*a*, is seated in the concave region 206 of the base member 204 and the bolts 105*a* or 105*b* are engaged to and translated into the internal base member engagement lumens 286*a*, 286*b* of the base member 204, the stabilizing rod, e.g., stabilizing rod 110, is similarly secured between the concave region 206 of the base member 204 and the proximal end 81*a* of the prosthesis bridge section 78, as illustrated in FIG. 6A.

Figure 7B:
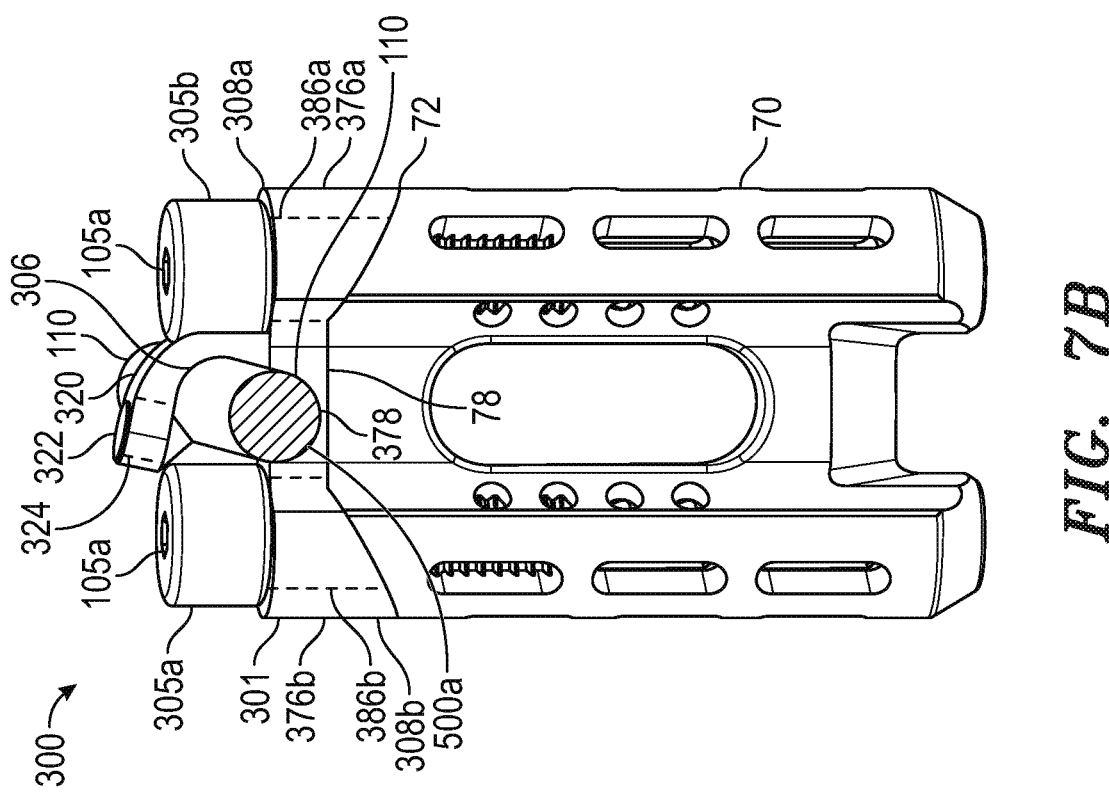
FIG. 7B is a front plan view of the pelvic structure stabilization sub-system prosthesis shown in FIG. 7A, in accordance with the invention.
Figure 7A:
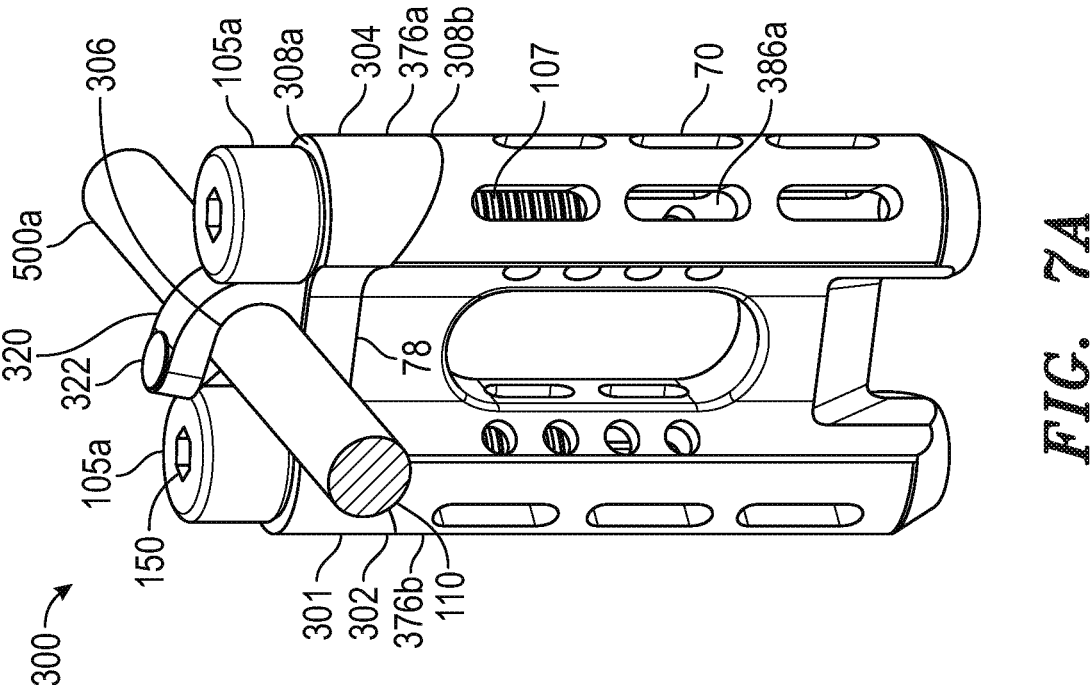
FIG. 7A is a perspective view of the pelvic structure stabilization sub-system prosthesis shown in FIG. 5A comprising a further embodiment of spine structure stabilization sub-system engagement means, in accordance with the invention.

Referring now to FIGS. 7A and 7B, there is shown yet another embodiment of a prosthesis system of the invention, i.e., first prosthesis system and/or second prosthesis system of the invention, (denoted "300") comprising prosthesis 70 and another embodiment of spine stabilization sub-system engagement means of the invention (denoted "301"), which, as illustrated in FIGS. 7A and 7B, is similarly adapted to engage (and cooperate with) spine structure stabilization sub-system 500*a*, i.e., a stabilizing bar 110 thereof.

As illustrated in FIGS. 7A and 7B, the spine stabilization sub-system engagement means 301 similarly comprises a base member 304 comprising proximal and distal ends 308*a*, 308*b*, and first and second elongated partially cylindrical sections 376*a*, 376*b* connected to a bridge section 378.

As further illustrated in FIGS. 7A and 7B, the first and second elongated partially cylindrical sections 376*a*, 376*b* of the base member 304 similarly comprise base member engagement lumens 386*a*, 386*b* that extend from the proximal end 308*a* to the distal end 308*b* of the base member 304.

In a preferred embodiment, the distal end 308*b* of the base member 304 is similarly sized and configured to conform to the shape of the proximal ends of the first and second elongated partially cylindrical sections 76*a*, 76*b* of the prosthesis 70.

As further illustrated in FIGS. 7A and 7B, in a preferred embodiment, the base member 304 comprises a pawl region 320 comprising a conical stabilizing rod engagement region 306 that is sized and configured to conform to and, hence, receive and seat a stabilizing rod of a spine stabilization sub-system of the invention, similarly, in this instance, stabilizing rod 110 of the spine stabilization sub-system 500*a*.

In some embodiments, the pawl region 320 is further configured to apply a retaining force to the stabilizing rod, e.g., stabilizing rod 110, whereby the stabilizing rod is secured to the base member 304.

As further illustrated in FIGS. 7A and 7B, in a preferred embodiment, the spine stabilization sub-system engagement means 301 further comprises a stabilizing rod conical securing pin 322 and the pawl region 320 further comprises a pawl region lumen 324 that is sized and configured to receive the stabilizing rod securing pin 322 therein.

According to the invention, when a stabilizing rod, in this instance, stabilizing rod 110, is positioned in the stabilizing rod engagement region 306 of the base member 304 and the stabilizing rod conical securing pin 322 is operatively positioned in the pawl region lumen 324, the stabilizing rod conical securing pin 322 abuts the stabilizing rod, as illustrated in FIG. 7B, and abates lateral movement of the stabilizing rod.

As additionally illustrated in FIGS. 7A and 7B, the spine stabilization sub-system engagement means 301 further similarly comprises bolts 105*a* or 105*b* that are sized and configured to slidably translate in and through the base member engagement lumens 386*a*, 386*b* and threadably engage the internal threads 87 of the internal prosthesis engagement member lumens 86*a*, 86*b* of the first and second elongated partially cylindrical sections 76*a*, 76*b* of the prosthesis 70, whereby the spine stabilization sub-system engagement means 301 can be securely engaged to the prosthesis 70.

Figure 8B:
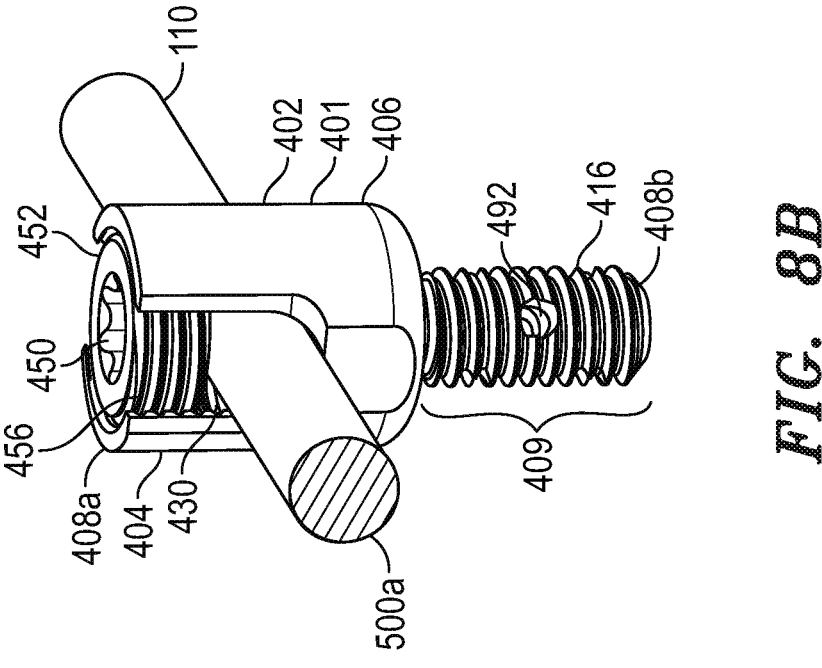
FIG. 8B is a perspective view of the spine stabilization sub-system engagement means shown in FIG. 8A, in accordance with the invention.
Figure 8A:
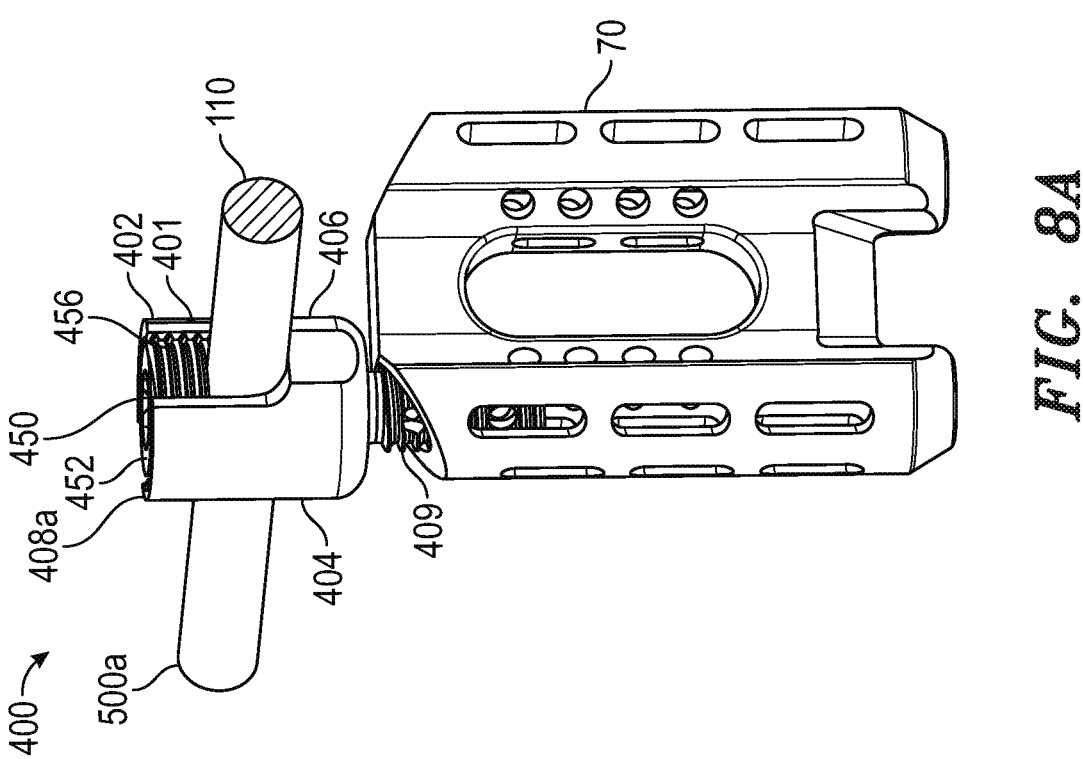
FIG. 8A is a perspective view of the pelvic structure stabilization sub-system prosthesis shown in FIG. 5A comprising a further embodiment of spine structure stabilization sub-system engagement means, in accordance with the invention.

Referring now to FIGS. 8A and 8B, there is shown a further embodiment of a prosthesis system of the invention, i.e., first prosthesis system and/or second prosthesis system of the invention, (denoted "400") comprising prosthesis 70 and another embodiment of spine stabilization sub-system engagement means of the invention (denoted "401"), which, as illustrated in FIGS. 8A and 8B, is similarly adapted to engage (and cooperate with) spine structure stabilization sub-system 500*a*, i.e., a stabilizing bar 110 thereof.

As illustrated in FIGS. 8A and 8B, in a preferred embodiment, the spine stabilization sub-system engagement means 400 comprises a threaded member 404 comprising proximal and distal ends 408*a*, 408*b*, a head region 406 disposed on the proximal end 408*a*, and a threaded region 409 disposed on the distal end 408*b*.

As further illustrated in FIGS. 8A and 8B, the threaded region 409 comprises at least one thread 416 that is sized and configured to engage and cooperate with the internal threaded regions 87 of the internal prosthesis engagement member lumens 86*a*, 86*b*, whereby the threaded member 404 and, hence, spine stabilization sub-system engagement means 401 can be securely engaged to prosthesis 70.

As further illustrated in FIGS. 8A and 8B, in a preferred embodiment, the head region 406 comprises a threaded stabilizing rod seat 430 that is sized and configured to receive and seat a stabilizing rod of a spine stabilization sub-system of the invention, similarly, in this instance, stabilizing rod 110 of the spine stabilization sub-system 500*a*, therein, as illustrated in FIGS. 8A and 8B.

As illustrated in FIG. 8B, in a preferred embodiment, the spine stabilization sub-system engagement means 400 further comprises a threaded securing member 452 that is sized and configured to engage and cooperate with the threads of the threaded stabilizing rod seat 430, whereby when a stabilizing rod of the spine structure stabilization sub-system, in this instance, stabilizing rod 110, is seated in the threaded stabilizing rod seat 430 and the threaded securing member 452 is also threadably engaged thereto, the threaded securing member 452 abuts and applies a retaining force to the stabilizing rod, i.e., stabilizing rod 110, securing the stabilizing rod in the threaded stabilizing rod seat 430 and, thereby, to spine stabilization sub-system engagement means 400.

In some embodiments of the invention, the head region 406 comprises a poly-axial or multi-axial head region that is adapted and configured to allow versatile angulation of the head region 406 to accommodate a multitude of positions to receive and seat the stabilizing rod.

Figure 9A:
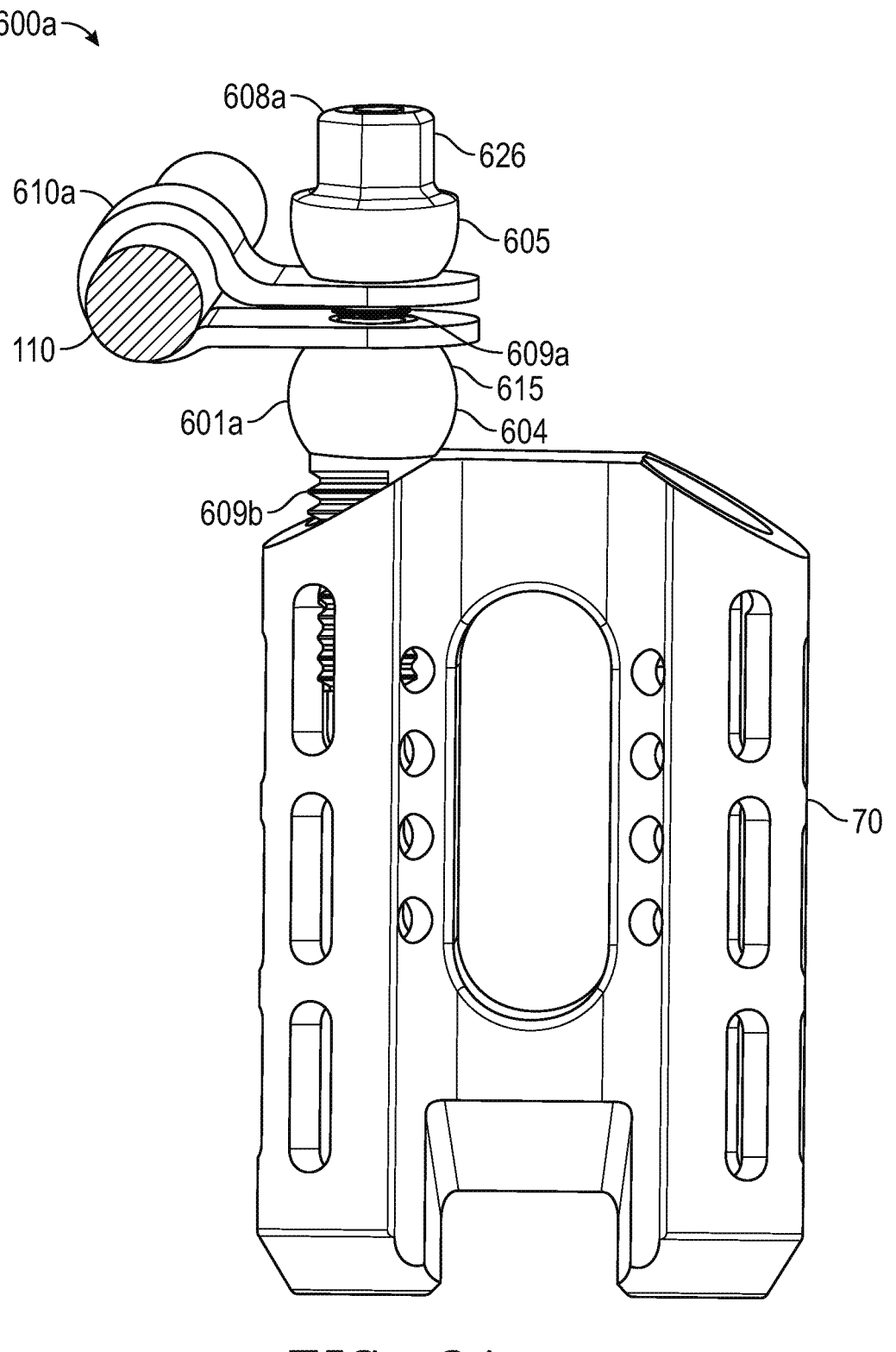
FIG. 9A is a perspective view of the pelvic structure stabilization sub-system prosthesis shown in FIG. 5A comprising a further embodiment of spine structure stabilization sub-system engagement means, in accordance with the invention.

Referring now to FIGS. 9A-9E, there is shown a further embodiment of a prosthesis system of the invention, i.e., first prosthesis system and/or second prosthesis system of the invention, (denoted "600*a*") comprising prosthesis 70 and another embodiment of spine stabilization sub-system engagement means of the invention (denoted "601*a*"), which, as illustrated in FIG. 9A, is similarly adapted to engage (and cooperate with) spine structure stabilization sub-system 500*a*, i.e., a stabilizing bar 110 thereof.

Figures 9B, 9C, 9D, 9E:
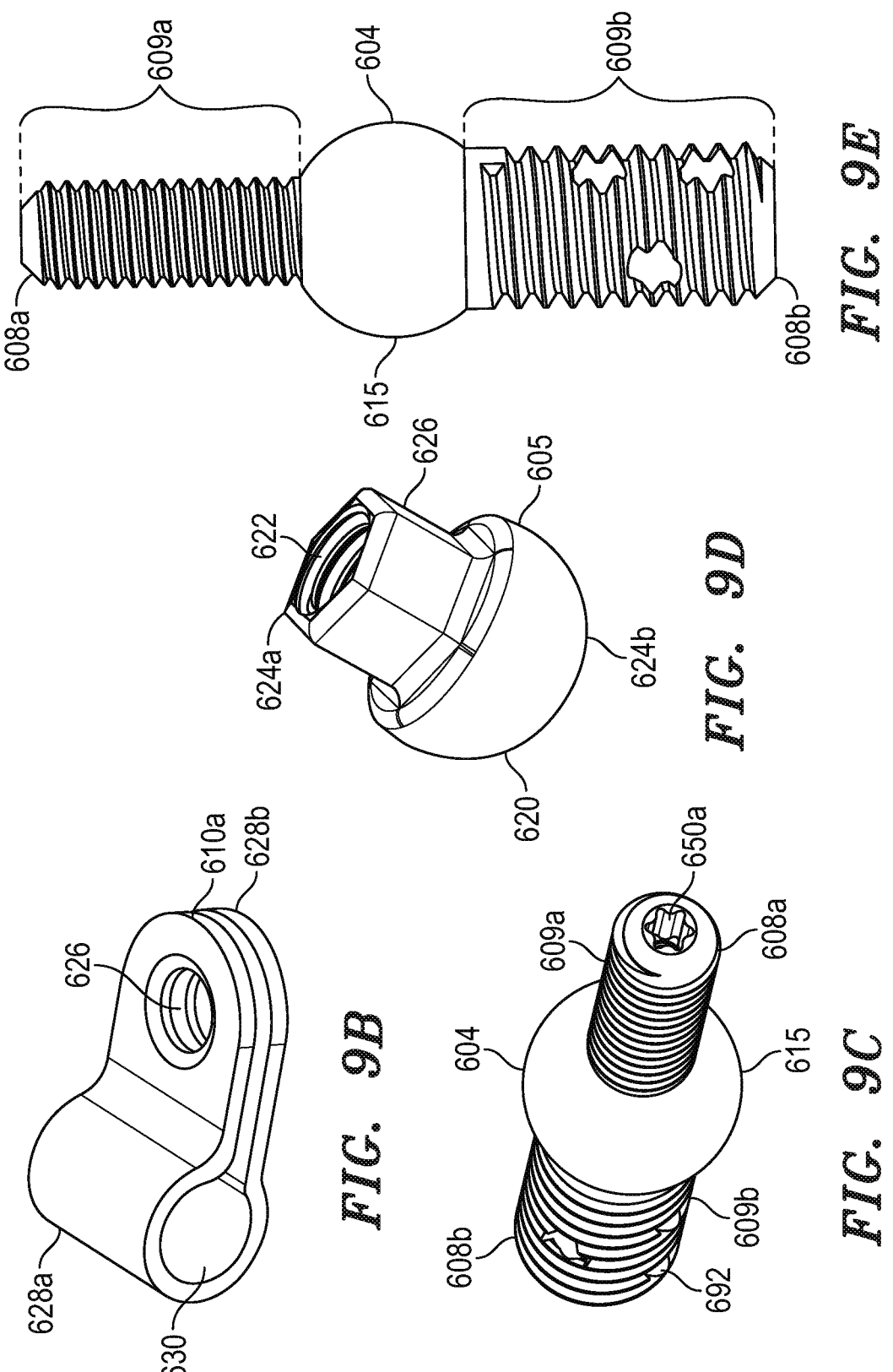
FIG. 9B is a perspective view of the spine structure stabilization sub-system engagement means stabilizing rod retainer clip shown in FIG. 9A, in accordance with the invention.
FIG. 9C is a perspective view of the spine structure stabilization sub-system engagement means threaded stud member shown in FIG. 9A, in accordance with the invention.
FIG. 9D is a perspective view of the spine structure stabilization sub-system engagement means nut member shown in FIG. 9A, in accordance with the invention.
FIG. 9E is a front plan view of the spine structure stabilization sub-system engagement means threaded stud member shown in FIG. 9C, in accordance with the invention.

As illustrated in FIGS. 9A and 9E, spine stabilization sub-system engagement means 600*a* comprises a threaded stud member 604 comprising proximal and distal ends 608*a*, 608*b*, a spherical medial region 615 disposed between the proximal and distal ends 608*a*, 608*b*, a first threaded region 609*a* disposed on the proximal end 608*a*, and a second threaded region 609*b* disposed on the distal end 608*b*; the second threaded region 609*b* sized and configured to engage the internal threaded regions 87 of the internal prosthesis engagement member lumens 86*a*, 86*b* of prosthesis 70, whereby, as discussed below, the spine stabilization sub-system engagement means 601*a* can be securely engaged to the prosthesis 70.

As illustrated in FIG. 9C, in a preferred embodiment, the proximal end 608*a* of the threaded stud member 604 similarly comprises an internal insertion tool engagement region 650*a*, which is configured to receive and cooperate with an external deployment and/or extraction tool or assembly. In some embodiments, the internal insertion tool engagement region 650*a* comprises a hexa-lobe configuration or region, as illustrated in FIG. 9C, which is adapted to receive and cooperate with an external "hexa-lobal" (or Torx head) tool or assembly.

As illustrated in FIGS. 9A and 9B, in a preferred embodiment, the spine stabilization sub-system engagement means 600*a* further comprises a stabilizing rod retainer member or clip 610*a* comprising proximal and distal ends 628*a*, 628*b*, a stabilizing rod seat region 630 disposed on the proximal end 628*a* that is sized and configured to receive a stabilizing rod, similarly, in this instance, stabilizing rod 110, therein, and a stud member engagement lumen 626 disposed on the distal end 628*b*; the stud member engagement lumen 626 sized and configured to receive the first threaded region 609*a* of the threaded stud member 604 therein and, hence, therethrough, as illustrated in FIG. 9A.

As further illustrated in FIG. 9A, in a preferred embodiment, the stabilizing rod retainer member 610*a* is adapted and configured to rotatably translate about the first threaded region 609*a* of the threaded stud member 604 to allow versatile angulation of the stabilizing rod seat region 630 to accommodate a multitude of positions to receive and seat the stabilizing rod.

As illustrated in FIGS. 9A and 9D, spine stabilization sub-system engagement means 600*a* further comprises a nut member 605 comprising proximal and distal ends 624*a*, 624*b*, a ball seat region 620 disposed on the distal end 624*b*, a hexagonal head region 626 disposed on the proximal end 624*a*, and an internal threaded stud engagement lumen 622 that extends from the proximal end 624*a* to the distal end 624*b*; the nut member 605 sized and configured to threadably engage the first threaded region 609*a* of the threaded stud member 604.

According to the invention, when threaded stud member 604 is threadably engaged to the internal threaded regions 87 of an internal prosthesis engagement member lumens 86*a* or 86*b* of prosthesis 70, a stabilizing rod of a spine stabilization sub-system of the invention, such as stabilizing rod 110 of the spine stabilization sub-system 500*a*, is seated in the stabilizing rod seat region 630 of retainer member or clip 610*a*, and nut member 605 is threadably engaged to the threaded stud member, the stabilizing rod, i.e., stabilizing rod 110, is securely connected to spine stabilization sub-system engagement means 601*a* and, thereby, prosthesis 70, as illustrated in FIG. 9A.

Figures 10A, 10B, 10C:
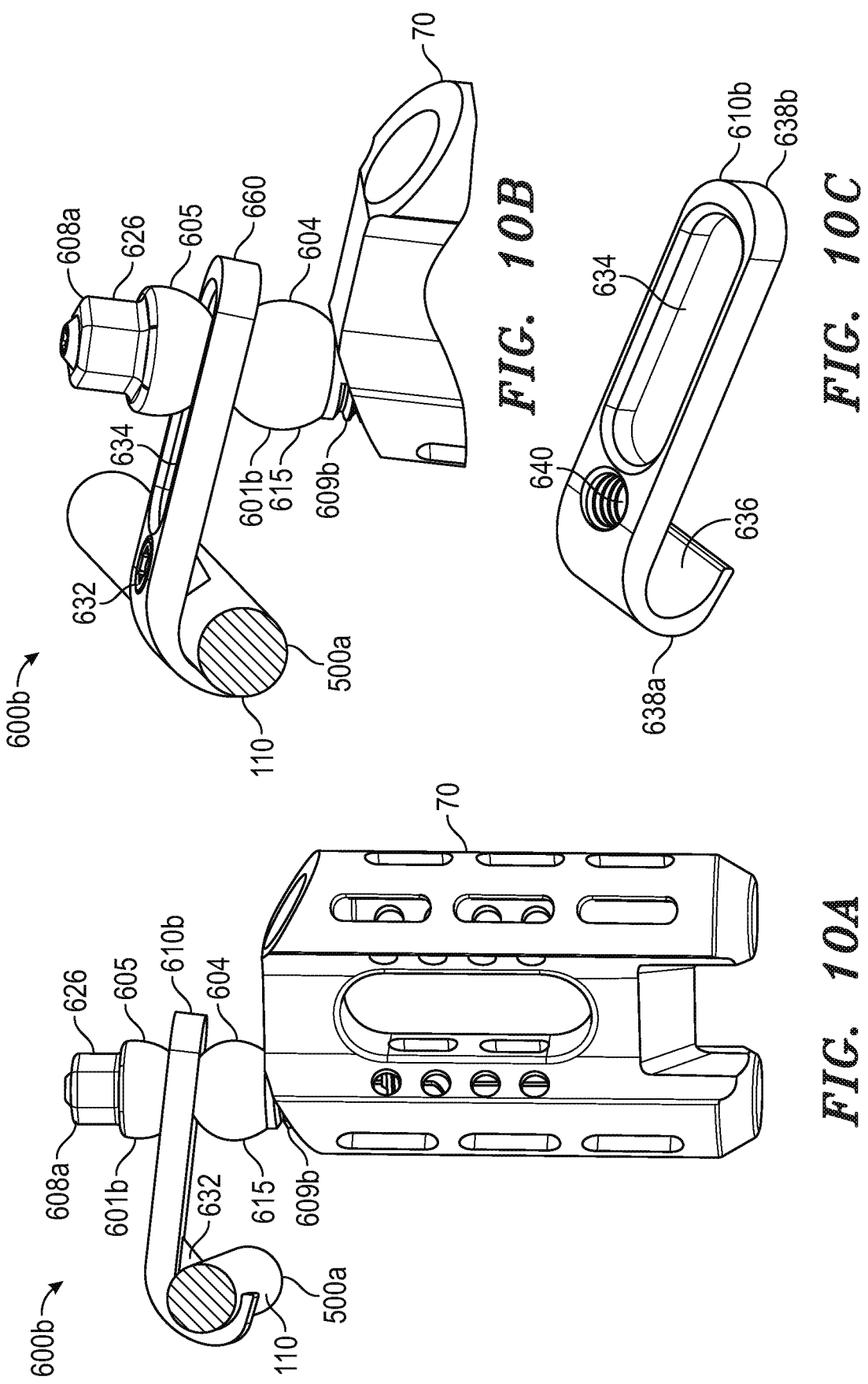
FIG. 10A is a perspective view of the pelvic structure stabilization sub-system prosthesis shown in FIG. 5A comprising a further embodiment of spine structure stabilization sub-system engagement means, in accordance with the invention.
FIG. 10B is a further perspective view of the spine structure stabilization sub-system engagement means shown in FIG. 10A, in accordance with the invention.
FIG. 10C is a perspective view of the spine structure stabilization sub-system engagement means stabilizing rod engagement member shown in FIGS. 10A and 10B, in accordance with the invention.

Referring now to FIGS. 10A-10C, there is shown another embodiment of a prosthesis system of the invention, i.e., first prosthesis system and/or second prosthesis system of the invention, (denoted "600*b*") comprising prosthesis 70 and another embodiment of spine stabilization sub-system engagement means 601*a* (now denoted "601*b*), which, as illustrated in FIGS. 10A and 10B, is similarly adapted to engage (and cooperate with) spine structure stabilization sub-system 500*a*, i.e., a stabilizing bar 110 thereof.

As illustrated in FIGS. 10A and 10B, in a preferred embodiment, the spine stabilization sub-system engagement means 601*b* similarly comprises a threaded stud member 604 and nut member 626.

However, as illustrated in FIGS. 10A-10C, in this embodiment, spine stabilization sub-system engagement means 601*b* comprises another embodiment of the stabilizing rod retainer member 610*a* (now denoted "610*b*").

As illustrated in FIG. 10C, the stabilizing rod retainer member 610*b* comprises proximal and distal ends 638*a*, 638*b*, a stabilizing rod seat region 636 disposed on the proximal end 638*a* that is sized and configured to receive a stabilizing rod, similarly, in this instance, stabilizing rod 110, therein, and a stud member engagement slot 634 disposed on the distal end 638*b*.

As illustrated in FIG. 10C, in a preferred embodiment, the distal end 638*b* of retainer member 610*b* further comprises a threaded engagement lumen 640 that is sized and configured to receive and seat a threaded conical pin member 632 that abuts the stabilizing rod, i.e., stabilizing rod 110, as illustrated in FIGS. 10A and 10B, and abates lateral movement of the stabilizing rod.

According to the invention, when threaded stud member 604 is similarly threadably engaged to the internal threaded regions 87 of an internal prosthesis engagement member lumens 86*a* or 86*b* of prosthesis 70, a stabilizing rod of a spine stabilization sub-system of the invention, such as stabilizing rod 110 of the spine stabilization sub-system 500*a*, is seated in the stabilizing rod seat region 636 of retainer member 610*b*, nut member 605 is threadably engaged to the threaded stud member 604 and threaded conical pin member 632 is threadably engaged to the retainer member 610*b*, the stabilizing rod, i.e., stabilizing rod 110, is securely connected to spine stabilization sub-system engagement means 601*b* and, thereby, prosthesis 70, as illustrated in FIGS. 10A and 10B.

Musculoskeletal Stabilization Systems

Referring now to FIGS. 11A-11B, 12A-12B, and 13A-13C, there are shown several embodiments of musculoskeletal stabilization systems of the invention.

Figure 11A:
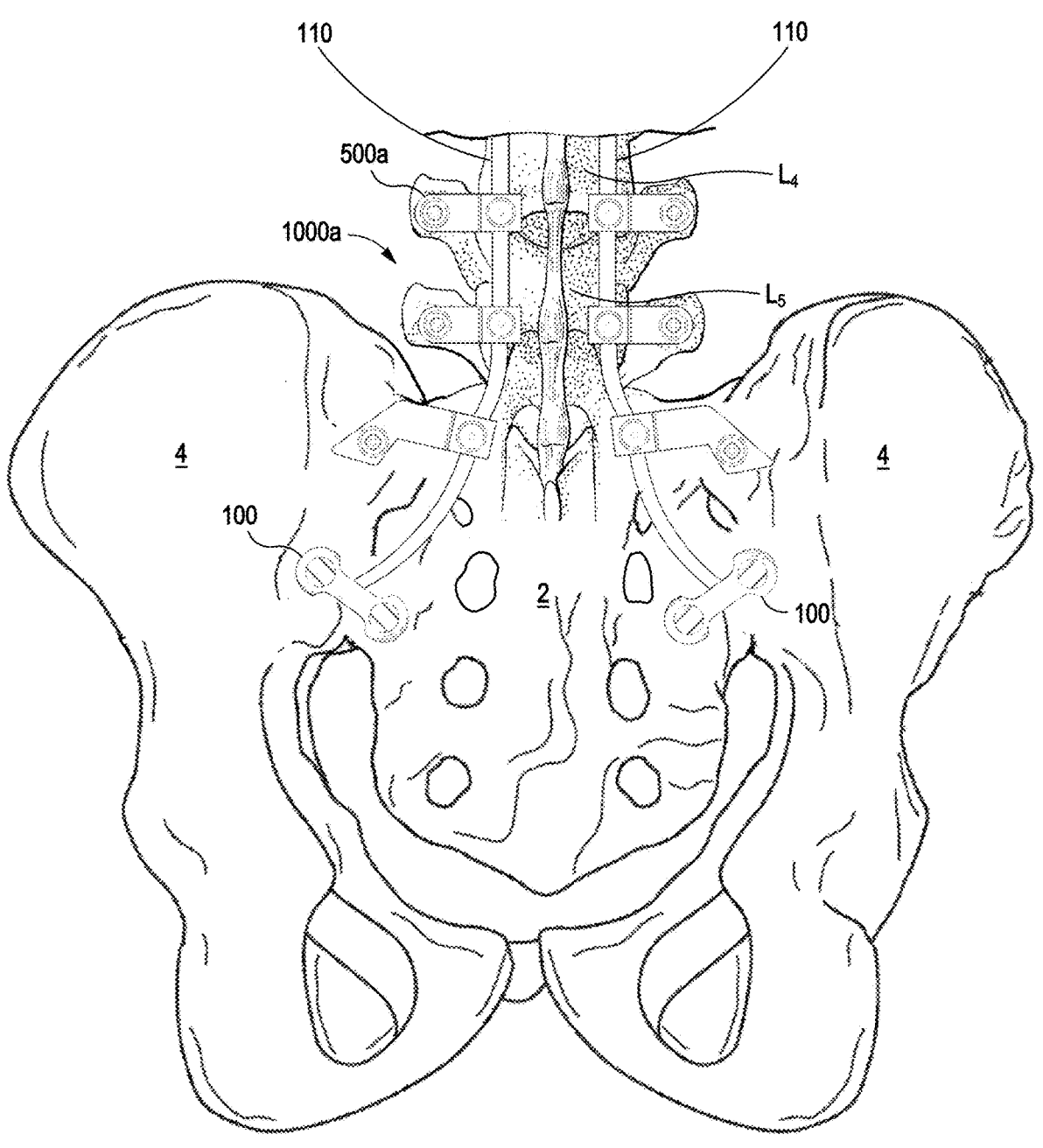
FIG. 11A is an illustration of one embodiment of a musculoskeletal stabilization system engaged to a subject's spine and pelvic girdle, in accordance with the invention.

Referring now to FIG. 11A, there is shown one embodiment of a musculoskeletal stabilization system 1000*a* of the invention, comprising spine structure stabilization sub-system 500*a* and pelvic structure stabilization sub-system 100 described above engaged to a subject's spine and pelvic girdle.

Figure 11B:
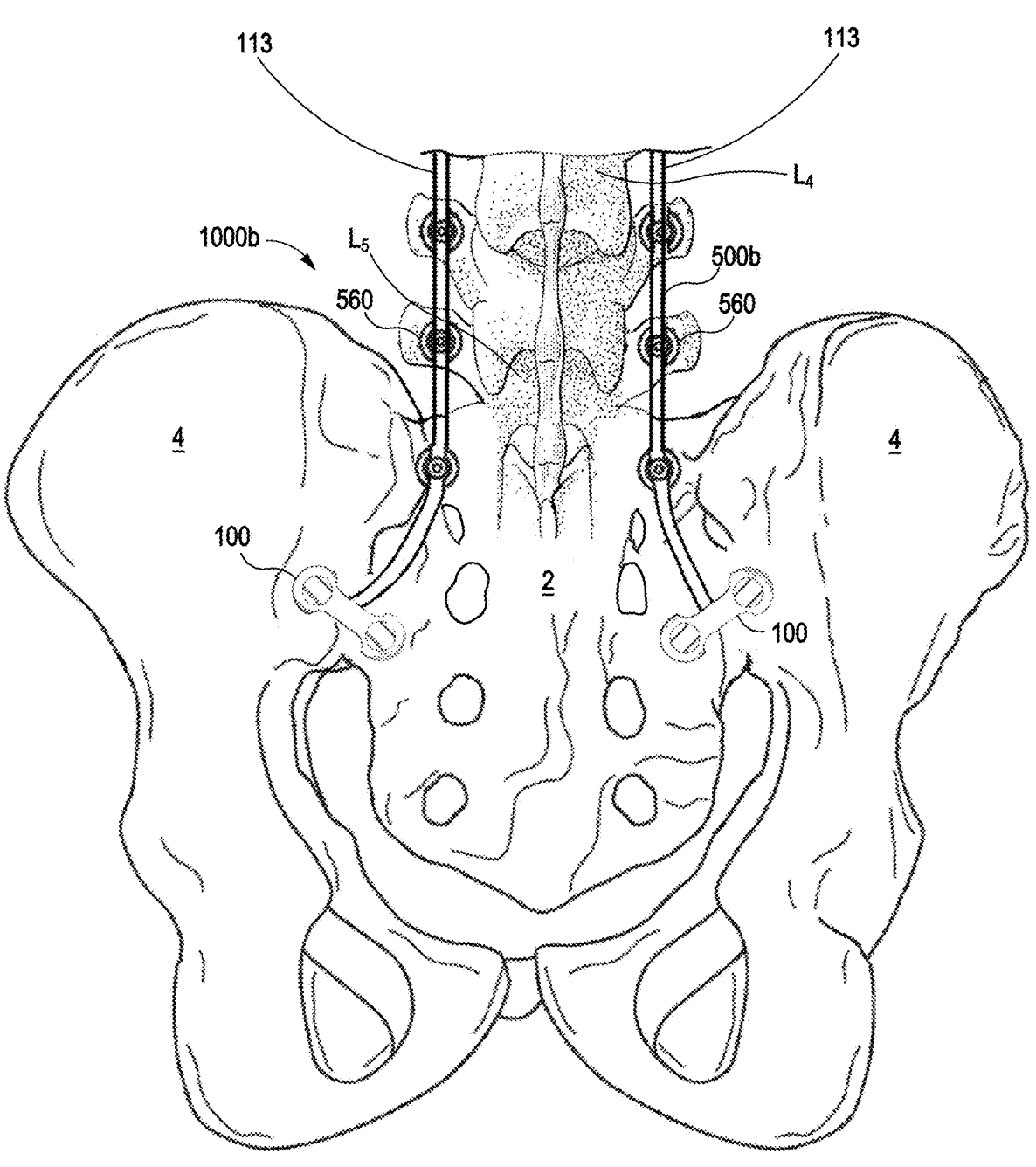
FIG. 11B is an illustration of another embodiment of a musculoskeletal stabilization system engaged to a subject's spine and pelvic girdle, in accordance with the invention.

Referring now to FIG. 11B, there is shown another embodiment of a musculoskeletal stabilization system 1000*b* of the invention, comprising another embodiment of spine structure stabilization sub-system 500*a* (now denoted "500*b*") and pelvic structure stabilization sub-system 100, which is similarly engaged to a subject's spine and pelvic girdle.

As illustrated in FIG. 11B, the spine stabilization sub-system 500*b* comprises stabilizing rods 113 and a plurality of bone screws 560, which are engaged to the stabilizing rods 113. As further illustrated in FIG. 11B, the bone screws 560 comprise head regions that are adapted and configured to retain and fixate the stabilizing rods 113.

Figure 12A:
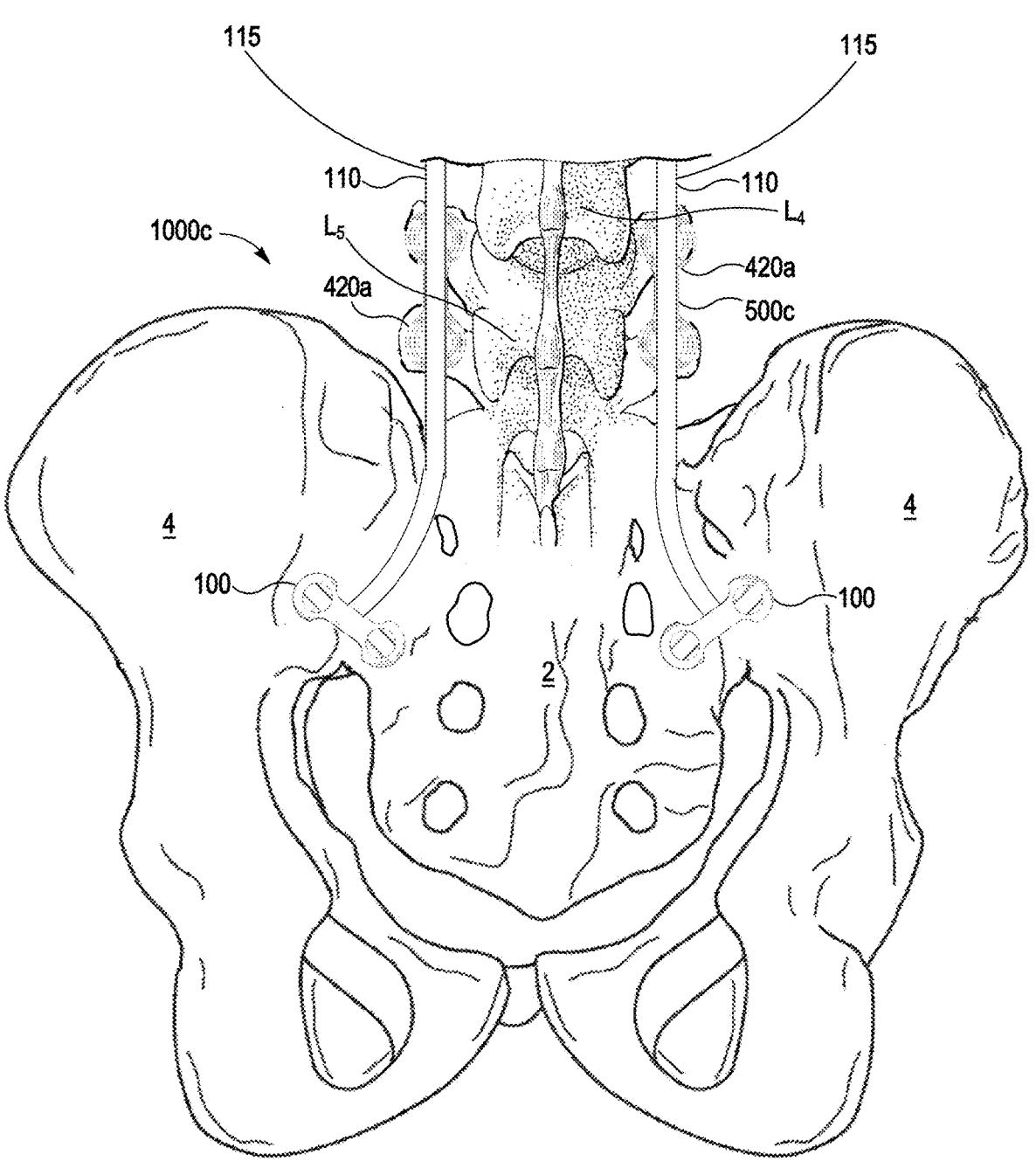
FIG. 12A is an illustration of a further embodiment of a musculoskeletal stabilization system engaged to a subject's spine and pelvic girdle, in accordance with the invention.
Figure 12B:
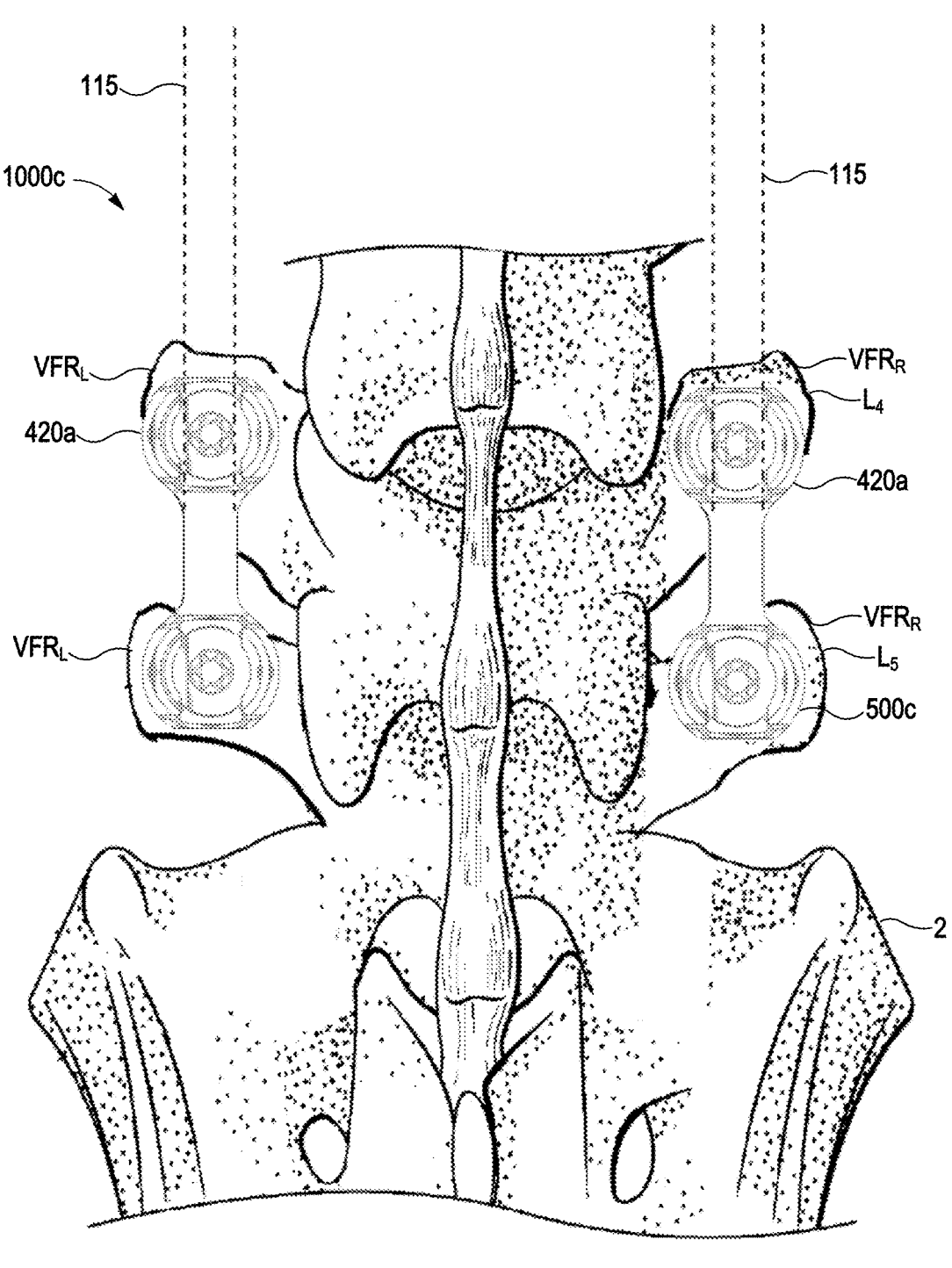
FIG. 12B is a further illustration of the musculoskeletal stabilization system shown in FIG. 12A, in accordance with the invention.

Referring now to FIGS. 12A and 12B, there is shown another embodiment of a musculoskeletal stabilization system 1000*c* of the invention, comprising another embodiment of a spine structure stabilization sub-system (denoted "500*c*") and pelvic structure stabilization sub-system 100, which is similarly engaged to a subject's spine and pelvic girdle.

As illustrated in FIGS. 12A and 12B, the spine stabilization sub-system 500*c* comprises stabilizing rods 115 and a plurality of vertebrae stabilizing sub-systems 420*a*, which are operatively engaged to the stabilizing rods 115.

As further illustrated in FIG. 12A, in a preferred embodiment, the spine stabilization sub-system 500*c* comprises vertebrae stabilizing sub-systems 420*a*, which are sized and configured to engage left vertebral facet regions (denoted "$VFR_L$") or right vertebral facet regions (denoted "$VFR_R$") of adjacent vertebrae that define an intervertebral joint, as illustrated in FIG. 12B.

In some embodiments, the vertebrae stabilizing sub-systems 420*a* comprise one of the aforementioned prosthesis systems.

According to the invention, the vertebrae stabilizing sub-systems 420*a* can comprise any suitable prosthesis system or combination thereof.

As further illustrated in FIG. 12B, in one embodiment of the invention, spine stabilization sub-system 500*c* comprises a pair of vertebrae stabilizing sub-systems 420*a*, including one vertebrae stabilizing sub-system 420*a* engaged to the left vertebral facet regions $VFR_L$ of $L_4$ and $L_5$ and another vertebrae stabilizing sub-system 420*a* engaged to the right vertebral facet regions $VFR_R$ of $L_4$ and $L_5$.

According to the invention, the spine stabilization sub-system 500*c* can comprise any number of vertebrae stabilizing sub-systems 420*a*.

In a preferred embodiment of the invention, the spine stabilization sub-system 500*c* comprises two (2) vertebrae stabilizing sub-systems 420*a* per intervertebral joint or per every two vertebral bodies, e.g., an $L_4$-$L_5$ intervertebral joint defined by $L_4$ and $L_5$ vertebral bodies.

Figure 13A:
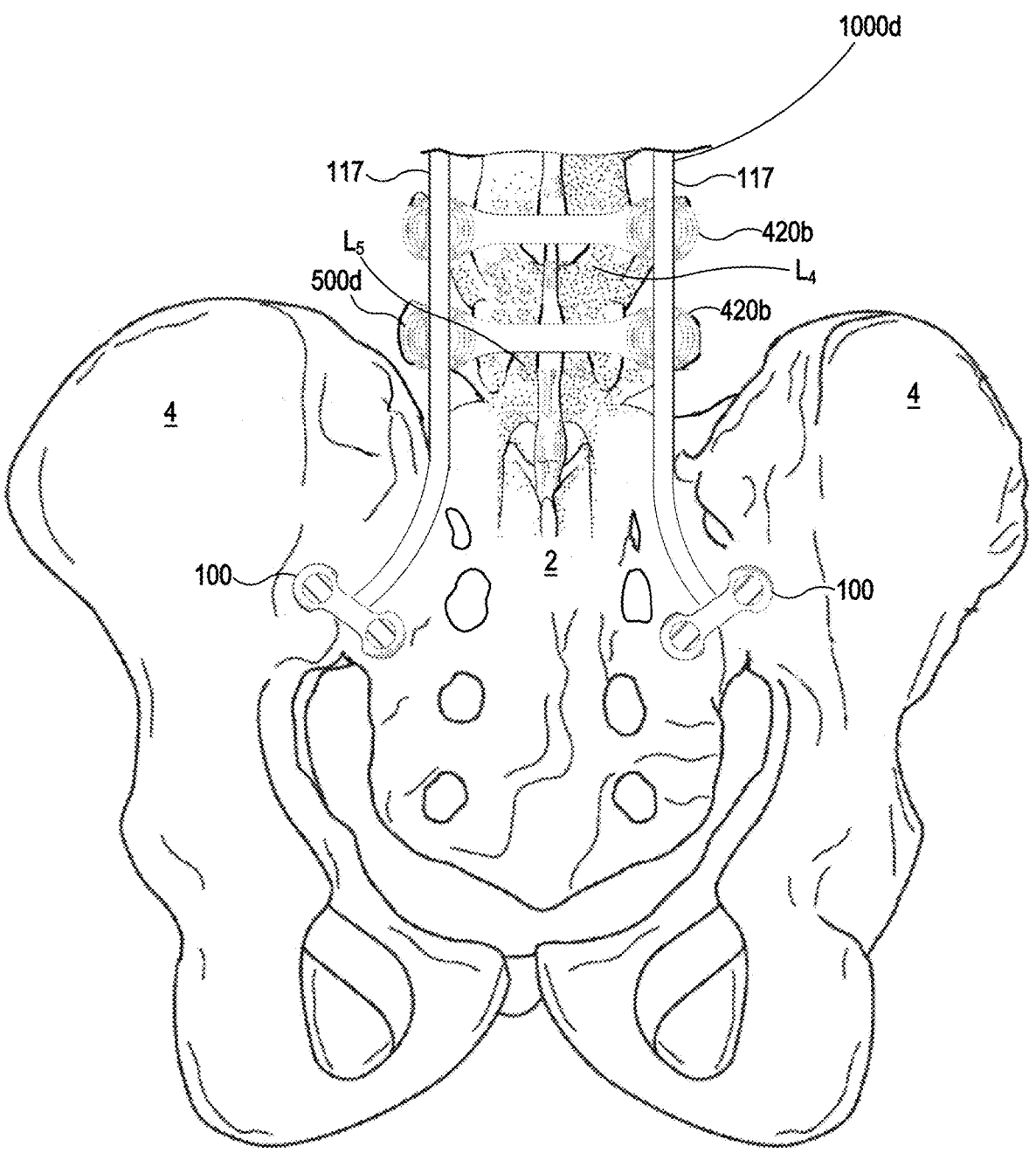
FIG. 13A is an illustration of a further embodiment of a musculoskeletal stabilization system engaged to a subject's spine and pelvic girdle, in accordance with the invention.
Figure 13B:
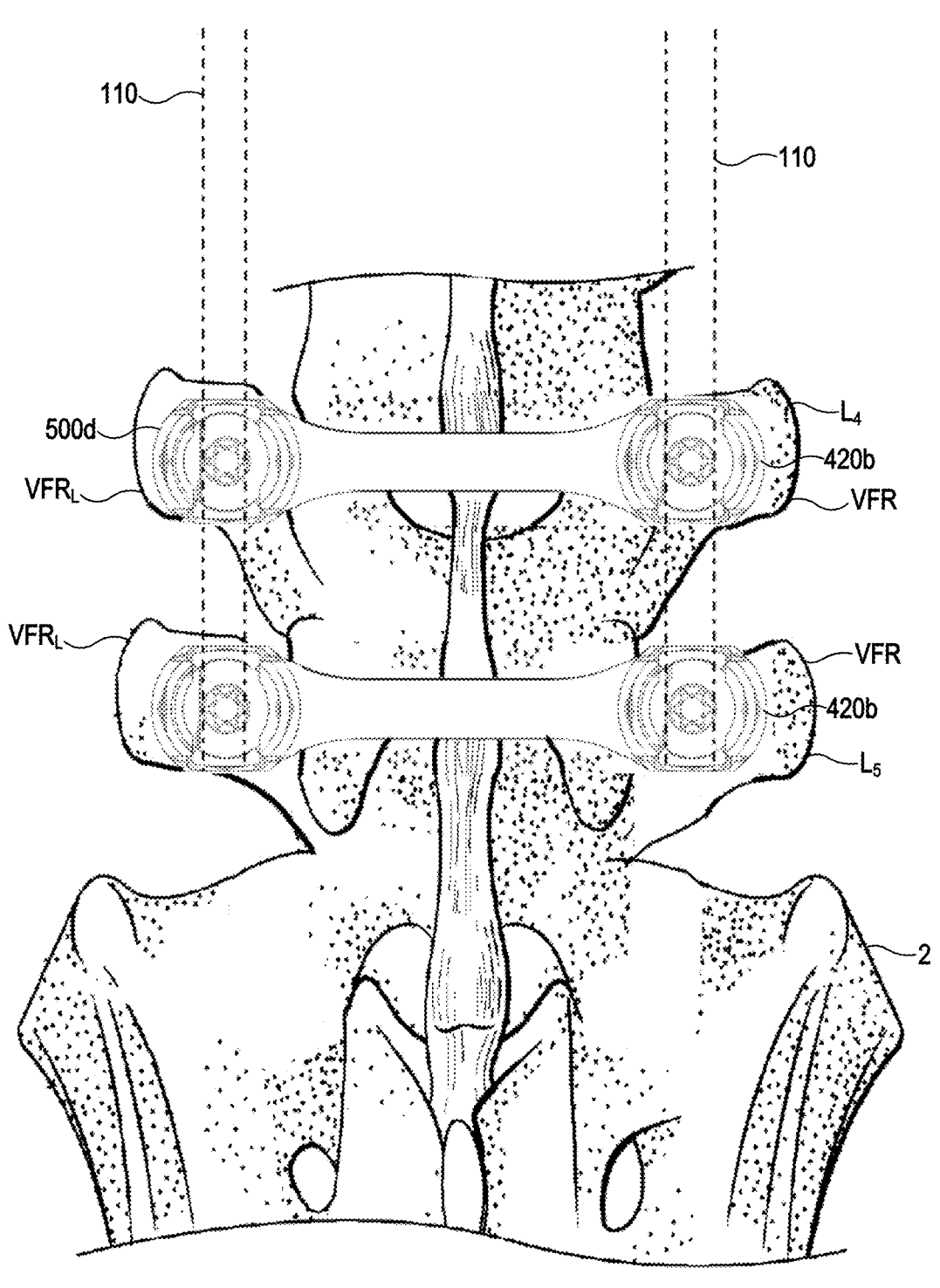
FIG. 13B is a further illustration of the musculoskeletal stabilization system shown in FIG. 13A, in accordance with the invention.

Referring now to FIGS. 13A-13C, there is shown another embodiment of a musculoskeletal stabilization system 1000*d* comprising another embodiment of a spine stabilization sub-system (denoted "500*d*").

As illustrated in FIGS. 13A-13C, the spine stabilization sub-system 500*d* comprises stabilizing rods 117 and another embodiment of vertebrae stabilizing sub-systems 420*a* (denoted "420*b*"), which are engaged to the stabilizing rods, and pelvic structure stabilization sub-system 100, which is similarly engaged to a subject's spine and pelvic girdle.

In a preferred embodiment, the vertebrae stabilizing sub-systems 420*b* comprise prosthesis system 400.

In a preferred embodiment, the prosthesis systems 400, i.e., prosthesis 70 thereof, extend across the vertebral body and engage left and right vertebral facet regions $VFR_L$ and $VFR_R$ of a single vertebral body.

According to the invention, the vertebrae stabilizing sub-systems 420*b* can similarly comprise any suitable combination of the aforementioned prosthesis systems.

As illustrated in FIG. 13B, in one embodiment of the invention, spine stabilization sub-system 500*d* comprises a pair of vertebrae stabilizing sub-systems 420*b*, including a first vertebrae stabilizing sub-system 420*b* engaged to the left and right vertebral facet regions $VFR_L$, $VFR_R$ of $L_4$ and a second vertebrae stabilizing sub-system 420*b* engaged to the left and right vertebral facet regions $VFR_L$, $VFR_R$ of $L_5$.

According to the invention, the spine stabilization sub-system 500*d* can similarly comprise any number of vertebrae stabilizing sub-systems 420*b*, i.e., prosthesis systems.

In a preferred embodiment of the invention, the spine stabilization sub-system 500*d* comprises one (1) vertebrae stabilizing sub-system 420*b* per vertebral body, e.g., an $L_5$ vertebral body.

Spine Structure Stabilization Systems

According to the invention, the stabilizing rods 110, 113, 115, and 117 of musculoskeletal structure stabilization systems 1000*a*, 1000*b*, 1000*c*, and 1000*d* can be sized, shaped, and configured to terminate at any point along the spine stabilization sub-system, i.e., sized, shaped, and configured to terminate at a desired vertebrae stabilizing sub-system 420*a* or 420*b* to form a spine structure stabilization system of the invention.

The stabilizing rods 113, 115, and 117 can similarly comprise various biocompatible materials, such as stainless steel or titanium (Ti).

The stabilizing rods 113, 115, and 117 can similarly comprise a shape memory alloy, such as Nitinol®.

Such structures, i.e., stabilizing rods 110, 113, 115, and 117 comprising Nitinol®, would be adapted to undergo a crystal phase transformation from a martensite crystal structure to an austenite crystal structure at a pre-defined transformation temperature and can be deformed (and, hence, shaped) at or above the transformation temperature, stay in the deformed configuration when the force(s) exerted to deform, i.e., shape, the structures have been removed, transition from the austenite crystal structure back to the martensite crystal structure when the structures are cooled below the transformation temperature, and then revert back to the original deformed configuration upon heating the structures above the transformation temperature, e.g., core temperature of a patient.

Thus, according to the invention, the Nitinol® stabilizing rods 110, 113, 115, and 117 of musculoskeletal stabilization systems 1000*a*, 1000*b*, 1000*c*, and 1000*d* can be pre-formed (or deformed to a desired shape) corresponding to a desired spine structure orientation, at or above the transformation temperature, cooled below the transformation temperature and employed as stabilizing rods of musculoskeletal stabilization systems 1000*a*, 1000*b*, 1000*c*, and 1000*d*, whereby, when Nitinol® stabilizing rods 110, 113, 115, and 117 are subjected to a temperature above the transformation temperature, e.g., core temperature of a patient, the stabilizing rods 110, 113, 115, and 117 will revert to the pre-formed shape, whereby the spine structure engaged thereto transitions from an undesirable spine structure orientation to the desired spine structure orientation, or induces a reversion force to the spine structure to induce transition from the undesirable spine structure orientation to the desired spine structure orientation.

As will be readily apparent to one skilled in the art, the musculoskeletal stabilization systems and apparatus of the invention, and methods employing same, provide numerous advantages compared to prior art systems and apparatus, and associated methods, for stabilizing spine and pelvic structures. Among the advantages are the following:

the provision of musculoskeletal stabilization systems, apparatus and methods that substantially reduce or eliminate the disadvantages associated with conventional systems and apparatus, and associated methods, for stabilizing spine and pelvic structures;

the provision of musculoskeletal stabilization systems and apparatus, and methods employing same, which effectively stabilize dysfunctional spine bone structures;

the provision of musculoskeletal stabilization systems and apparatus, and methods employing same, which effectively ameliorate pain associated with spine bone structure dysfunction;

the provision of musculoskeletal stabilization systems and apparatus, and methods employing same, which effectively stabilize dysfunctional pelvic bone structures;

the provision of musculoskeletal stabilization systems and apparatus, and methods employing same, which effectively ameliorate pain associated with pelvic bone structure dysfunction; particularly, SI joint dysfunction;

the provision of musculoskeletal stabilization systems and apparatus, and methods employing same, which effectively stabilize dysfunctional spine and pelvic bone structures;

the provision of musculoskeletal stabilization systems comprising SI joint stabilization sub-systems comprising prostheses adapted to induce remodeling of damaged osseous tissue and regeneration of new osseous tissue; and the provision of improved spine stabilization systems that are adapted to induce transition of spine structures from an undesirable spine structure orientation to a desired spine structure orientation when engaged thereto.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A musculoskeletal stabilization system, comprising:

a spine structure stabilization sub-system and a pelvic structure stabilization sub-system, said spine structure stabilization sub-system comprising a plurality of bone-engaging anchoring assemblies, and first and second elongate stabilizing rods, each of said plurality of bone-engaging anchoring assemblies adapted to engage vertebral bone structures of said subject's spine, said first and second elongate stabilizing rods adapted to be positioned on opposite sides of said subject's sagittal plane, said pelvic structure stabilization sub-system comprising first and second prosthesis systems, said first prosthesis system comprising a first prosthesis adapted to be inserted into a first sacroiliac (SI) joint of a subject, said second prosthesis system comprising a second prosthesis adapted to be inserted into a second SI joint of a subject, said first prosthesis and said second prosthesis each comprising first and second elongated partially cylindrical sections connected to a first bridge section, said first bridge section comprising first bridge section proximal and distal ends, said first bridge section distal end comprising a first tapered region configured and adapted to disrupt at least first articular cartilage and cortical bone, said first elongated partially cylindrical section comprising a first elongated partially cylindrical section proximal end, a first elongated partially cylindrical section distal end, and a first internal lumen that extends through said first elongated partially cylindrical section, said first internal lumen comprising first internal threads disposed on said first elongated partially cylindrical section proximal end, said second elongated partially cylindrical section comprising a second elongated partially cylindrical section proximal end, a second elongated partially cylindrical section distal end, and a second internal lumen that extends through said second elongated partially cylindrical section, said second internal lumen comprising second internal threads disposed on said second elongated partially cylindrical section proximal end, said first prosthesis system further comprising first spine structure stabilization sub-system engagement means adapted to engage at least said first internal threads of said first elongated partially cylindrical section of said first prosthesis and said spine structure stabilization sub-system, said second prosthesis system further comprising second spine structure stabilization sub-system engagement means adapted to engage at least said first internal threads of said first elongated partially cylindrical section of said second prosthesis and said spine structure stabilization sub-system.

2. The musculoskeletal stabilization system of claim 1, wherein at least said first internal lumen of said first elongated partially cylindrical section of said first prosthesis is adapted to receive a first osteogenic composition therein.

3. The musculoskeletal stabilization system of claim 2, wherein said first elongated partially cylindrical section of said first prosthesis further comprises a first plurality of slots in communication with said first lumen of said first elongated partially cylindrical section of said first prosthesis, said first plurality of slots adapted to allow said first osteogenic composition to be dispersed out of said first internal lumen of said first elongated partially cylindrical section of said first prosthesis and delivered to said first SI joint when said first prosthesis is said inserted therein.

4. The musculoskeletal stabilization system of claim 1, wherein at least said first internal lumen of said first elongated partially cylindrical section of said first prosthesis is adapted to receive a second osteogenic composition therein.

5. The musculoskeletal stabilization system of claim 4, wherein said first elongated partially cylindrical section of said second prosthesis further comprises a first plurality of slots in communication with said first lumen of said first elongated partially cylindrical section of said second prosthesis, said first plurality of slots adapted to allow said second osteogenic composition to be dispersed out of said first internal lumen of said first elongated partially cylindrical section of said second prosthesis and delivered to said second SI joint when said second prosthesis is said inserted therein.

6. The musculoskeletal stabilization system of claim 1, wherein said first prosthesis is adapted to be delivered to and said inserted into said first SI joint via a first posterior trajectory, and said second prosthesis is adapted to be delivered to and said inserted into said second SI joint via a second posterior trajectory.

7. The musculoskeletal stabilization system of claim 1, wherein said first spine structure stabilization sub-system engagement means of said first prosthesis system is adapted to engage said first elongate stabilizing rod of said spine structure stabilization sub-system, and said second spine structure stabilization sub-system engagement means of said second prosthesis system is adapted to engage said second elongate stabilizing rod of said spine structure stabilization sub-system.

* * * * *